(12) United States Patent
Armstrong et al.

(10) Patent No.: US 11,944,354 B2
(45) Date of Patent: Apr. 2, 2024

(54) SPINAL IMPLANT SYSTEM AND METHOD

(71) Applicant: WARSAW ORTHOPEDIC INC., Warsaw, IN (US)

(72) Inventors: Rex W. Armstrong, Cordova, TN (US); David A. Mire, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 185 days.

(21) Appl. No.: 17/163,902

(22) Filed: Feb. 1, 2021

(65) Prior Publication Data
US 2021/0153906 A1 May 27, 2021

Related U.S. Application Data

(62) Division of application No. 15/432,704, filed on Feb. 14, 2017, now abandoned.

(51) Int. Cl.
*A61B 17/70* (2006.01)
*A61B 17/86* (2006.01)

(52) U.S. Cl.
CPC ........ *A61B 17/705* (2013.01); *A61B 17/7032* (2013.01); *A61B 17/7035* (2013.01); *A61B 17/7049* (2013.01); *A61B 17/8665* (2013.01); *A61B 2017/867* (2013.01)

(58) Field of Classification Search
CPC .............. A61B 17/7049; A61B 17/705; A61B 17/7052
See application file for complete search history.

(56) References Cited

U.S. PATENT DOCUMENTS

| | | | |
|---|---|---|---|
| 5,207,678 A | 5/1993 | Harms et al. | |
| 5,575,792 A | 11/1996 | Errico et al. | |
| 5,609,593 A | 3/1997 | Errico et al. | |
| 5,609,654 A | 3/1997 | Le et al. | |
| 5,630,817 A | 5/1997 | Rokegem et al. | |
| 5,643,263 A | 7/1997 | Simonson | |
| 5,676,665 A * | 10/1997 | Bryan ............... | A61B 17/7034 606/252 |
| 5,797,911 A | 8/1998 | Sherman et al. | |
| 5,885,285 A | 3/1999 | Simonson | |
| 5,947,967 A | 9/1999 | Barker | |
| 6,074,391 A | 6/2000 | Metz-Stavenhagen et al. | |
| 6,280,442 B1 | 8/2001 | Barker et al. | |
| 6,520,962 B1 | 2/2003 | Taylor et al. | |
| 6,562,038 B1 | 5/2003 | Morrison | |
| 6,572,618 B1 | 6/2003 | Morrison | |
| 6,579,292 B2 | 6/2003 | Taylor | |
| 6,648,887 B2 | 11/2003 | Ashman | |
| 6,685,705 B1 | 2/2004 | Taylor | |
| 6,755,830 B2 | 6/2004 | Minfelde et al. | |

(Continued)

*Primary Examiner* — Jan Christopher L Merene
(74) *Attorney, Agent, or Firm* — Sorell, Lenna & Schmidt, LLP

(57) ABSTRACT

A spinal construct includes a coupling member including a first mating surface engageable with an existing fastener implant. The existing fastener implant defines a cavity configured for disposal of an existing spinal rod implant. A connector is engageable with the existing fastener implant and has a rod extending therefrom. A locking member is engageable with a second mating surface of the coupling member. Systems, surgical instruments, implants and methods are disclosed.

20 Claims, 26 Drawing Sheets

(56) References Cited

U.S. PATENT DOCUMENTS

| | | | |
|---|---|---|---|
| 6,872,209 B2 | 3/2005 | Morrison | |
| 7,066,939 B2 | 6/2006 | Taylor | |
| 8,585,741 B2 | 11/2013 | Gabelberger et al. | |
| 8,992,575 B1 | 3/2015 | Di Lauro et al. | |
| 9,314,274 B2 | 4/2016 | Amstutz et al. | |
| 9,402,663 B2 | 8/2016 | Peterson et al. | |
| 10,786,285 B2 | 9/2020 | Stein et al. | |
| 2002/0029040 A1* | 3/2002 | Morrison | A61B 17/7011 606/292 |
| 2008/0177323 A1* | 7/2008 | Null | A61B 17/705 606/267 |
| 2010/0049253 A1* | 2/2010 | Miller | A61B 17/7041 606/264 |
| 2011/0184412 A1* | 7/2011 | Scifert | A61B 17/68 606/60 |
| 2012/0109210 A1* | 5/2012 | Baker | A61B 17/705 606/264 |
| 2012/0130436 A1* | 5/2012 | Haskins | A61B 17/7032 606/301 |
| 2013/0096617 A1* | 4/2013 | Ballard | A61B 17/7049 606/278 |
| 2013/0184760 A1* | 7/2013 | Ballard | A61B 17/7038 606/279 |
| 2018/0214187 A1* | 8/2018 | Shoshtaev | A61B 17/7064 |
| 2018/0228518 A1* | 8/2018 | Carruth | A61B 17/866 |

* cited by examiner

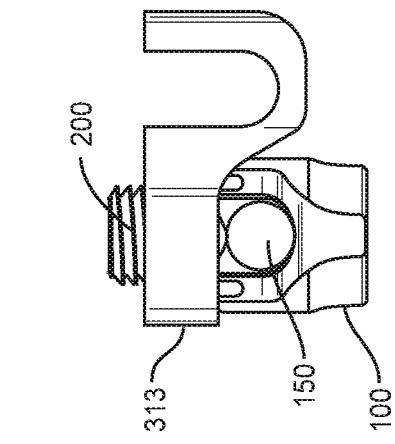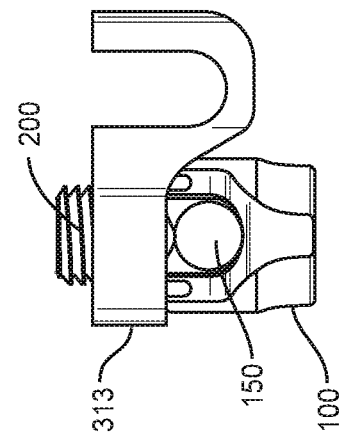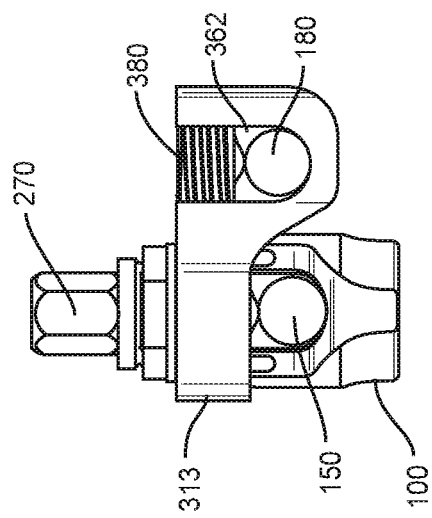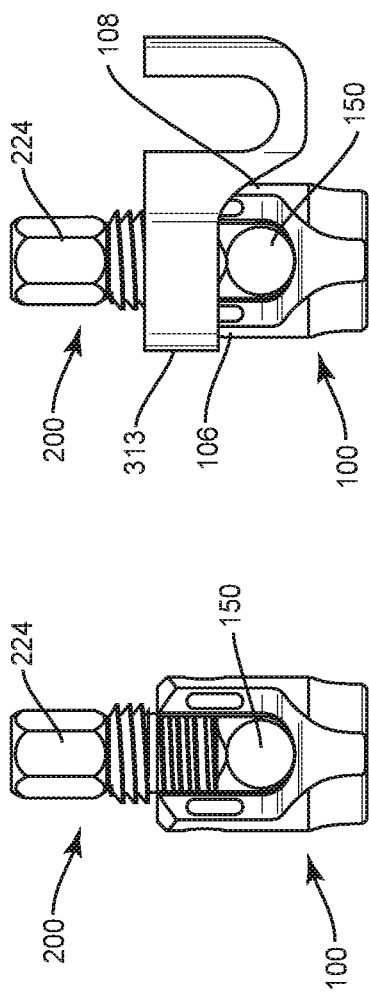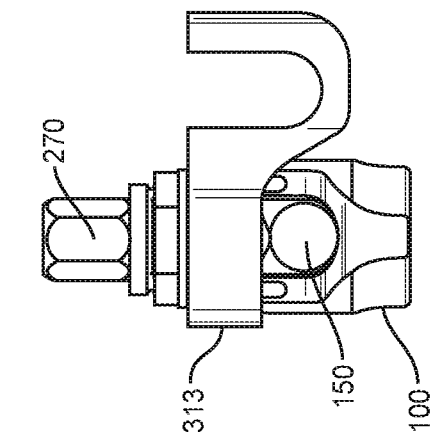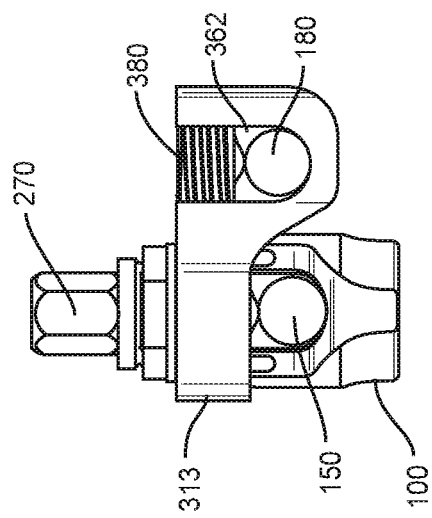

SPINAL IMPLANT SYSTEM AND METHOD

CROSS-REFERENCE TO RELATED APPLICATION

This application is a divisional of U.S. patent application Ser. No. 15/432,704, filed Feb. 14, 2017, which is expressly incorporated herein by reference, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct includes a coupling member including a first mating surface engageable with an existing fastener implant. The existing fastener implant defines a cavity configured for disposal of an existing spinal rod implant. A connector is engageable with the existing fastener implant and has a rod extending therefrom. A locking member is engageable with a second mating surface of the coupling member. In some embodiments, systems, surgical instruments, implants and methods are disclosed.

BRIEF DESCRIPTION OF THE DRAWINGS

The present disclosure will become more readily apparent from the specific description accompanied by the following drawings, in which:

FIG. 18 is a side view of components of one embodiment of a system in accordance with the principles of the present disclosure;

FIG. 19 is a side view of components of one embodiment of a system in accordance with the principles of the present disclosure;

FIG. 20 is a side view of components of one embodiment of a system in accordance with the principles of the present disclosure;

FIG. 21 is a side view of components of one embodiment of a system in accordance with the principles of the present disclosure;

FIG. 22 is a side view of components of one embodiment of a system in accordance with the principles of the present disclosure;

FIG. 23 is a side view of components of one embodiment of a system in accordance with the principles of the present disclosure;

DETAILED DESCRIPTION

Figure 1:
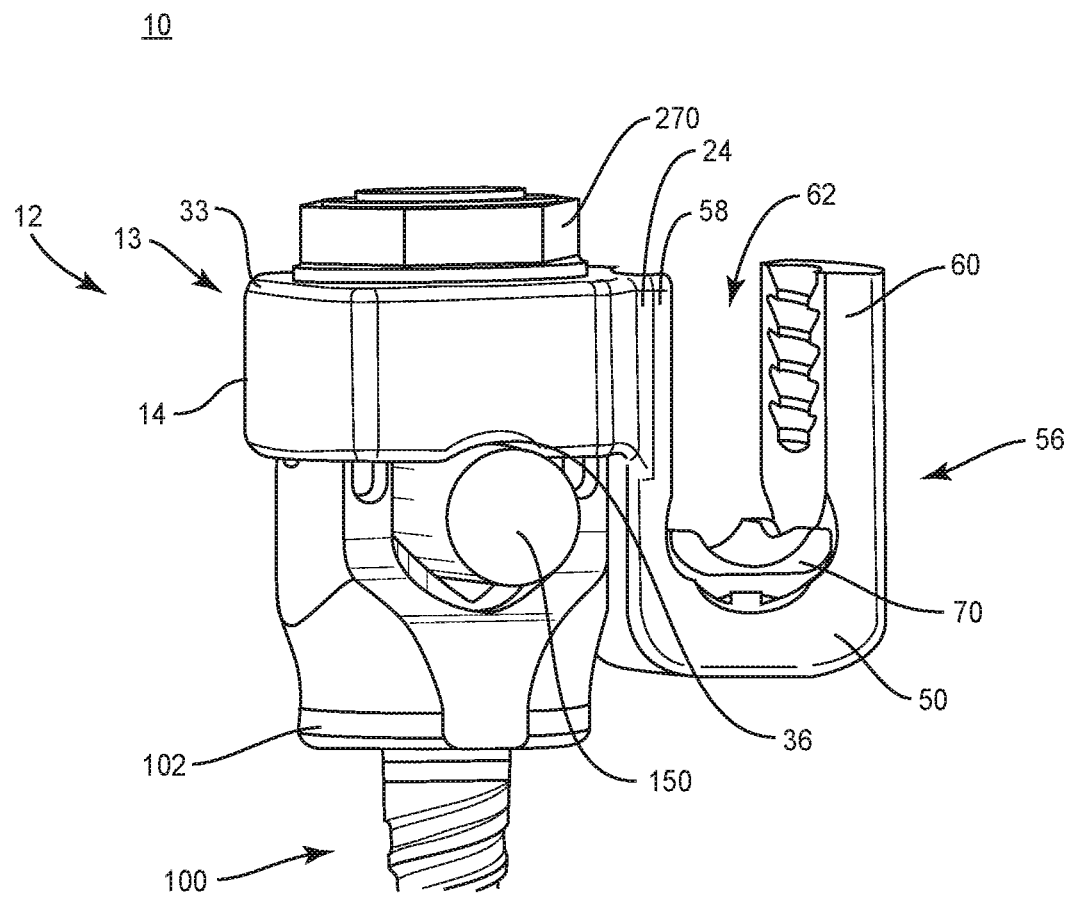
FIG. 1 is a perspective view of components of one embodiment of a system in accordance with the principles of the present disclosure.
Figure 2:
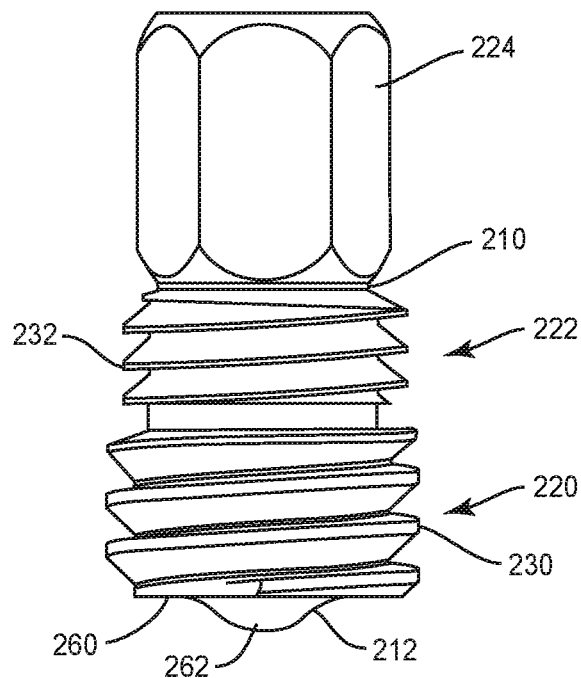
FIG. 2 is a side view of components of one embodiment of a system in accordance with the principles of the present disclosure.
Figure 3:
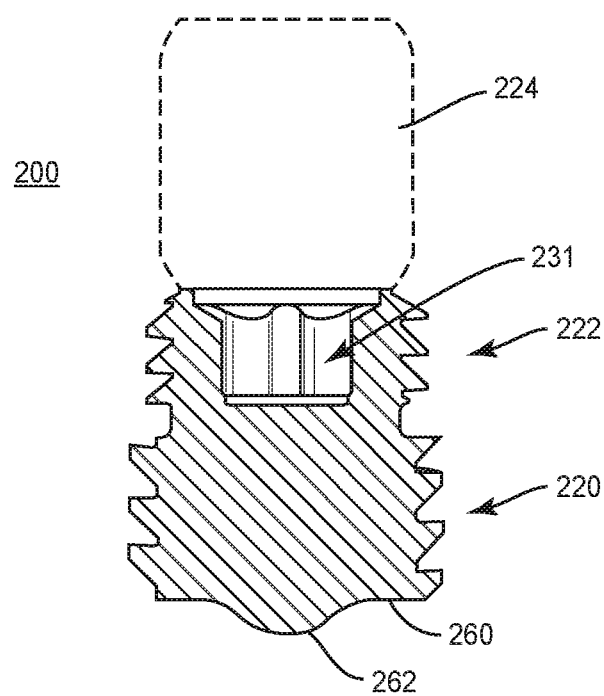
FIG. 3 is a cross section view of the components shown in FIG. 2.
Figure 4:
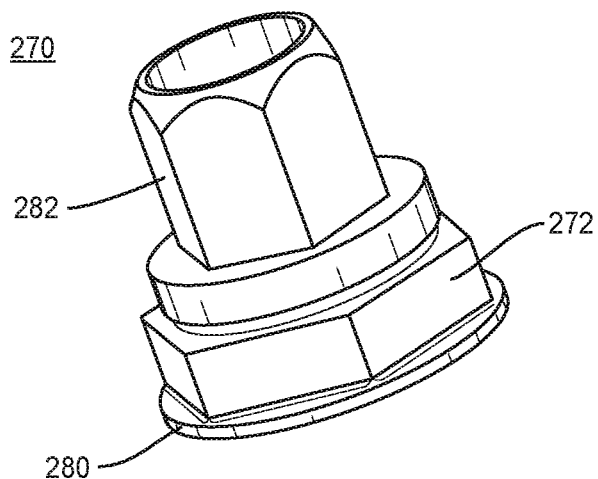
FIG. 4 is a perspective view of components of one embodiment of a system in accordance with the principles of the present disclosure.
Figure 5:
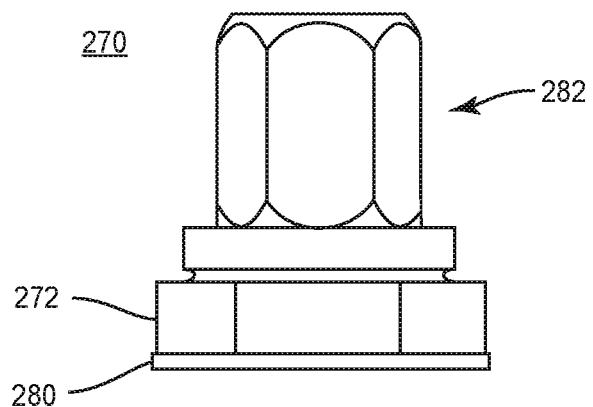
FIG. 5 is a side view of the components shown in FIG. 4.
Figure 6:
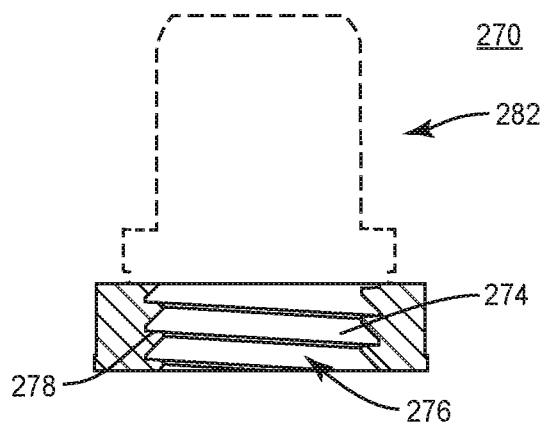
FIG. 6 is a cross section view of the components shown in FIG. 4.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a spinal construct comprising a connector. In some embodiments, the present surgical system includes a spinal construct comprising a screw to rod connector. In some embodiments, the present surgical system includes a spinal construct comprising one or more revision minimally invasive surgical connectors. In some embodiments, the present surgical system includes a spinal construct that can be employed with a method for treating a spine with a plurality of spinal rods, which can be used to hold a spine until fusion occurs. In some embodiments, the present surgical system includes a spinal construct that can be employed with a method for treating a spine, which includes a pedicle subtraction osteotomy, a transforaminal lumbar interbody fusion (TLIF) and/or long constructs in heavy patients.

In some embodiments, the present surgical system includes a spinal construct comprising a bone screw and a spinal rod connector. In some embodiments, the present surgical system includes a spinal construct that can be employed with a method for treating a spine, which includes attaching a secondary rod to an existing pedicle screw. In some embodiments, the spinal construct includes a double-threaded setscrew (DTS), a connector and a nut, which allows the secondary rod to attach to the spinal construct. In some embodiments, a bottom thread of the DTS mates with the pedicle screw and allows it to function as the original setscrew. In some embodiments, the connector mates with the DTS and the pedicle screw head and includes geometry to receive the secondary rod. In some embodiments, the nut threads onto a top thread of the DTS and clamps the connector to the top of the pedicle screw.

In some embodiments, the present surgical system includes a spinal construct that can be employed with a method for treating a spine, which includes revision of a fractured rod such that the existing setscrew is removed and the DTS is inserted on the screw above and below the fracture. The connectors are placed over the DTS and a multi-axial screw (MAS) and secured with nuts. In some embodiments, a new rod can be installed into the connectors bridging the fracture of the rod regardless of the proximity of the existing pedicle screws.

In some embodiments, the present surgical system includes a spinal construct that can be employed with a method for treating a spine, which includes connecting a second rod to a pedicle screw construct by changing the setscrew and installing the connector, which allows contouring the secondary rod independently of a primary rod.

In some embodiments, the spinal construct includes a primary rod disposed with a MAS, FAS or a SAS pedicle screw and a screw to rod connector. In some embodiments, a double-hex break-off nut and a double-thread setscrew connect the components. In some embodiments, the connector comprises a secondary rod and setscrew receiver. In some embodiments, the nut clamps the connector to the primary rod via the double-thread setscrew. In some embodiments, the bottom of the connector contacts the primary rod to distribute the load between the rod and the setscrew. In some embodiments, there is a gap between the double-threaded setscrew and the rod such that the double-threaded setscrew does not clamp the rod to the bone screw, however, the nut attaches the connector to the pedicle screw.

In some embodiments, the spinal construct comprises a flanged double-thread setscrew. In some embodiments, the top nut clamps the connector to the flange on the setscrew via the top thread on the setscrew. In some embodiments, the load from the connector is distributed to the setscrew via the flange. In some embodiments, the connector can rotate on the flange allowing the rods to be non-parallel.

In some embodiments, the spinal construct comprises a connector setscrew with breakoff and a bearing surface. In some embodiments, the spinal construct comprises a MAS setscrew with stem and a breakoff hex feature. In some embodiments, the breakoff hex feature shears to expose the stem. In some embodiments, the stem guides the connector setscrew. In some embodiments, the connector fits over the MAS and rotates into position. In some embodiments, the connector includes hooks on each side to grasp an underside of the primary rod. In some embodiments, the connector includes a setscrew mating thread.

In some embodiments, the present surgical system includes a spinal construct and is employed with a method for treating a spine. In some embodiments, the method includes the step of disposing a MAS setscrew with the MAS head. In some embodiments, the method includes the step of placing a connector on the MAS over the setscrew and resting on the MAS head such that there is a small gap between the bottom of the rod and the hooks. In some embodiments, the method includes the step of fully tightening the MAS setscrew and shearing the hex. In some embodiments, the method includes the step of threading the connector setscrew into the connector to bear against the mating surface of the MAS setscrew. In some embodiments, the method includes the step of forcing the hooks to contact the bottom of the rod. In some embodiments, the method includes the step of fully tightening the connector setscrew and shearing off the breakoff feature. In some embodiments, the method includes the step of placing the secondary rod such that the secondary rod load is shared between the setscrew and the rod.

In some embodiments, the spinal construct includes a spline assembly that allows for rotation, which may include secondary rod angulation, for example in a coronal orientation, before the setscrew is tightened and interdigitate when the setscrew is tightened to lock the spinal construct. In some embodiments, the spinal construct includes a spline assembly that allows for rotation, which may include secondary rod angulation, for example in a sagittal orientation, before the setscrew is tightened and interdigitate when the setscrew is tightened to lock the spinal construct. In some embodiments, the spinal construct includes a secondary rod receiver with fixed coronal angle offset. In some embodiments, the spinal construct includes a secondary rod receiver with fixed sagittal angle offset.

In some embodiments, the spinal construct includes a revision connector configured to attach to one or more existing spinal constructs implanted with a body. In some embodiments, the spinal construct can be employed in a revision surgery to extend an existing screw and rod construct. In some embodiments, the spinal construct can be employed in a revision surgery to connect an existing spinal construct and extend the existing spinal construct to span one or more spinal levels.

In some embodiments, the present surgical system includes a spinal construct that can be employed in a revision surgery to connect to an existing rod implanted with a body. In some embodiments, the spinal construct and the existing spinal construct comprise an extension. In some embodiments, the present surgical system includes a spinal construct that can be employed in a revision surgery to connect to an existing bone screw and rod construct through a minimally invasive approach. In some embodiments, the present surgical system includes a spinal construct having an adjustable rod geometry such that the rod is top-loaded to the connector after delivery of the connector to a surgical site.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a" "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-11, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with existing constructs, which may include fastener implants and/or spinal rod implants attached with vertebrae, in a revision surgery to manipulate tissue and/or correct a spinal disorder, as described herein. In some embodiments, one or more of the components of spinal implant system 10 can be employed in a revision surgery to connect an existing spinal construct and extend, revise or repair the existing spinal construct to span one or more spinal levels. Spinal implant system 10 comprises a spinal construct 12. In some embodiments, one or more components of spinal construct 12 are configured to extend an existing spinal rod implant with or without removing the existing rod implant. In some embodiments, existing spinal constructs may include one or more implants connected or fixed with tissue in a prior or different surgical procedure, separate in time and/or over a duration of time in the same surgical procedure.

Spinal construct 12 includes a connector 13. Connector 13 includes a body 14 that defines an axis X1. Body 14 includes a wall 24 that defines a sleeve 33. Sleeve 33 extends between a surface 26 and a surface 28. In some embodiments, surfaces 26, 28 include a planar configuration and extend perpendicular to axis X1. Sleeve 33 includes an inner surface 30 that defines a cavity 32. Cavity 32 is configured for disposal of a receiver 102 of an existing fastener implant, such as, for example, a multi-axial fastener 100, as described herein. In some embodiments, the existing fastener implant may include sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

Cavity 32 includes a substantially rectangular cross section. In some embodiments, cavity 32 may have various cross section configurations, such as, for example, oval, oblong, triangular, rectangular, square, polygonal, irregular, uniform, non-uniform, variable and/or tapered. In some embodiments, surface 30 may include gripping elements or surface 30 may be, for example, rough, arcuate, undulating, mesh, porous, semi-porous, dimpled and/or textured to facilitate engagement with fastener 100.

Figure 11:
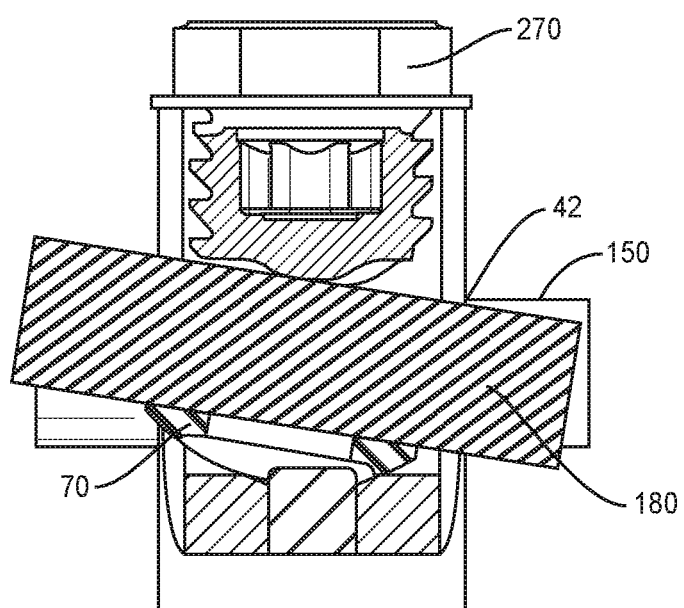
FIG. 11 is a cross section view of components of one embodiment of a system in accordance with the principles of the present disclosure.

A portion of surface 28 disposed along wall 24 defines a recess 36. Recess 36 includes a concave configuration, as shown in FIG. 1. Recess 36 is configured to conform to a shape of an existing implant, such as, for example, a spinal rod 150, as described herein. A portion of surface 28 disposed along wall 24 defines a recess 42, as shown in FIG. 11. Recess 42 includes a concave configuration and conforms to the shape of spinal rod 150, as described herein. Recess 42 is disposed in alignment with recess 36 to facilitate disposal of spinal rod 150 with connector 13. Wall 24 includes one or more arcuate surfaces configured for a mating engagement with arms of receiver 102, as described herein.

Figure 7:
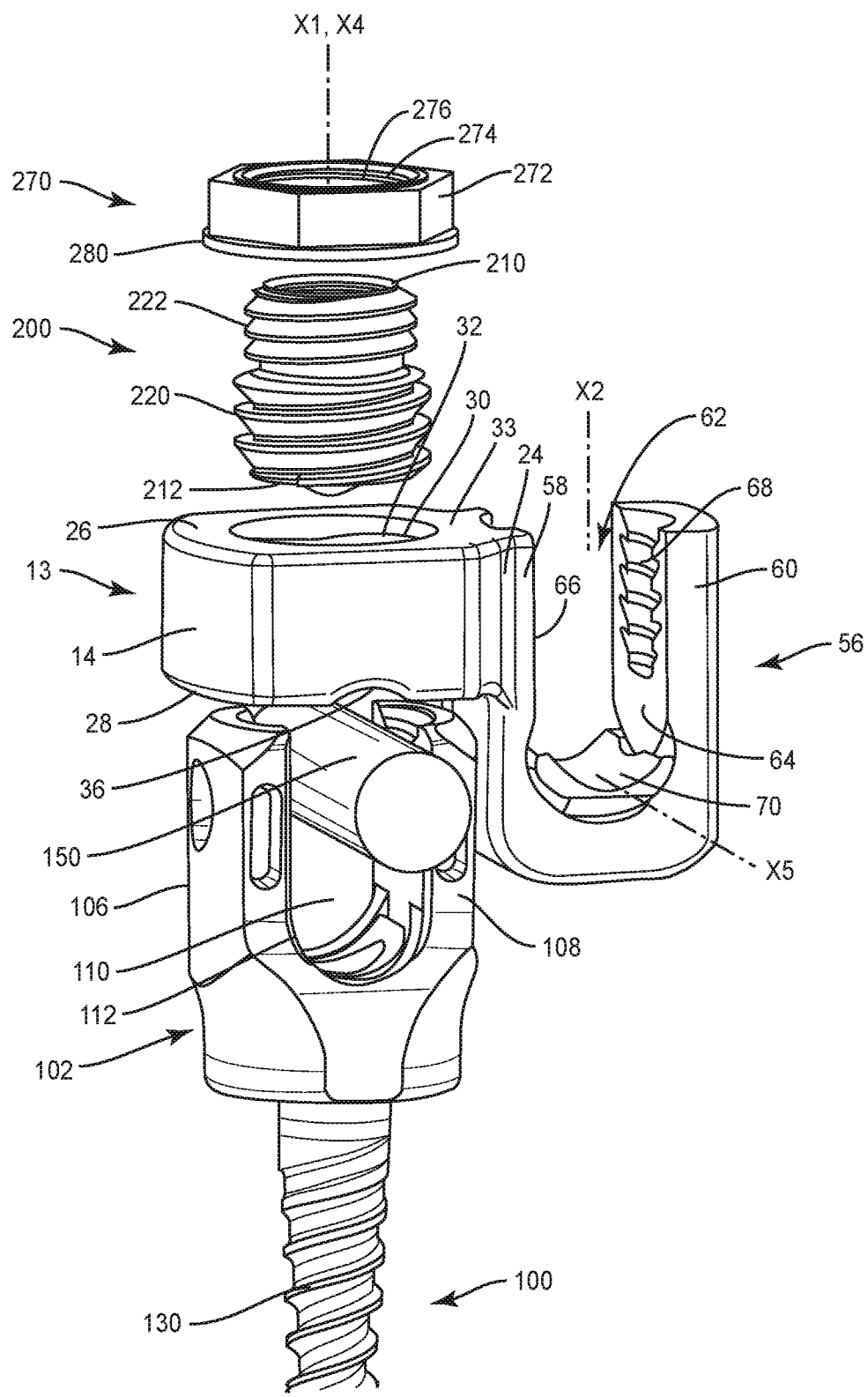
FIG. 7 is a perspective view of components of one embodiment of a system in accordance with the principles of the present disclosure with parts separated.

Connector 13 includes a body 50 that includes a receiver 56, as shown in FIG. 1. Receiver 56 includes a pair of spaced apart arms 58, 60 that define an implant cavity, such as, for example, a passageway 62. Passageway 62 is configured for disposal of a spinal implant, such as, for example, a rod 180 to extend and/or revise an existing spinal construct, as described herein. Passageway 62 is configured for top loading of spinal rod 180. In some embodiments, passageway 62 can be positioned for alternate loading orientations, such as, for example, side, lateral and/or positions disposed transverse to axis X1. Arms 58, 60 each extend parallel to an axis X2, as shown in FIG. 7. In some embodiments, arm 58 and/or arm 60 may be disposed at alternate orientations, relative to axis X2, such as, for example, transverse, perpendicular and/or other angular orientations such as acute or obtuse, coaxial and/or may be offset or staggered. Arms 58, 60 each include an arcuate outer surface extending between a pair of side surfaces. In some embodiments, at least one of the outer surfaces and the side surfaces of arms 58, 60 have at least one recess or cavity therein configured to receive an insertion tool, compression instrument and/or instruments for manipulating connector 13.

Passageway 62 is substantially U-shaped. In some embodiments, all or only a portion of passageway 62 may have alternate cross section configurations, such as, for example, closed, V-shaped, W-shaped, oval, oblong triangular, square, polygonal, irregular, uniform, non-uniform, offset, staggered, and/or tapered. Receiver 56 includes an inner surface 64. A portion of surface 64 includes a thread form 66 located adjacent arm 58 and a thread form 68 located adjacent arm 60. Thread forms 66, 68 are each configured for engagement with a coupling member, such as, for example, a set screw (not shown), to retain rod 180 within passageway 62. In some embodiments, surface 64 may be disposed with a set screw in alternate fixation configurations, such as, for example, friction fit, pressure fit, locking protrusion/recess, locking keyway and/or adhesive. In some embodiments, all or only a portion of surface 64 may have alternate surface configurations to enhance engagement with a spinal rod and/or a set screw such as, for example, rough, arcuate, undulating, mesh, porous, semi-porous, dimpled and/or textured. The set screw is configured for engagement with rod 180 to facilitate fixation and/or locking of rod 180 with receiver 56. The set screw is disposable with receiver 56 between a non-locking orientation, such that rod 180 is translatable relative to connector 13 and a locked orientation, such that the set screw fixes rod 180 with connector 13.

Figure 8:
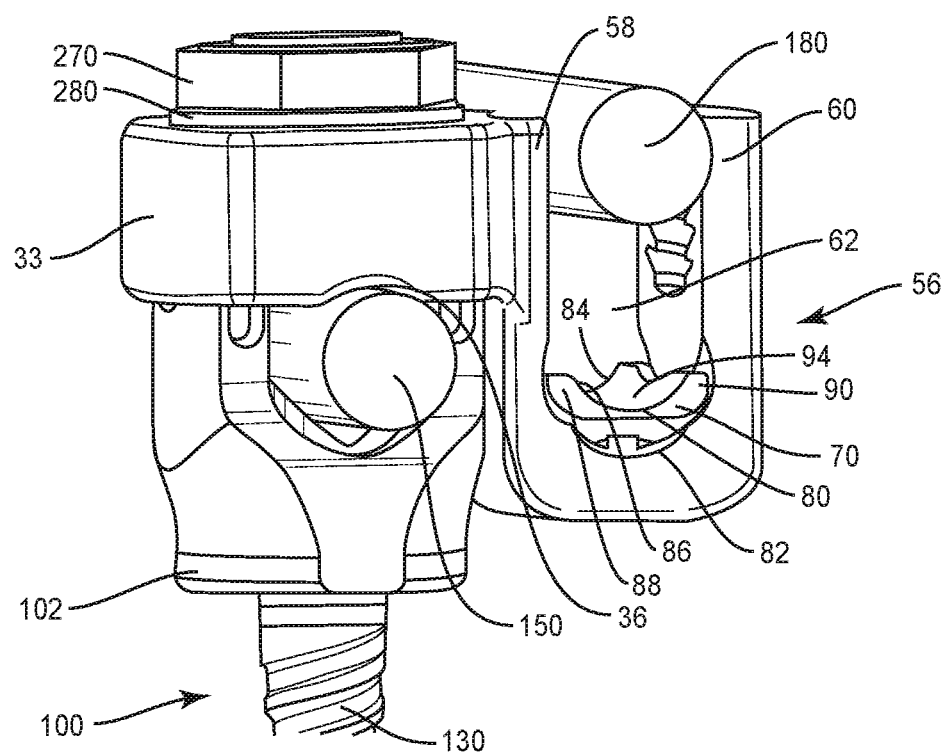
FIG. 8 is a perspective view of the components of one embodiment of a system in accordance with the principles of the present disclosure.
Figure 9:
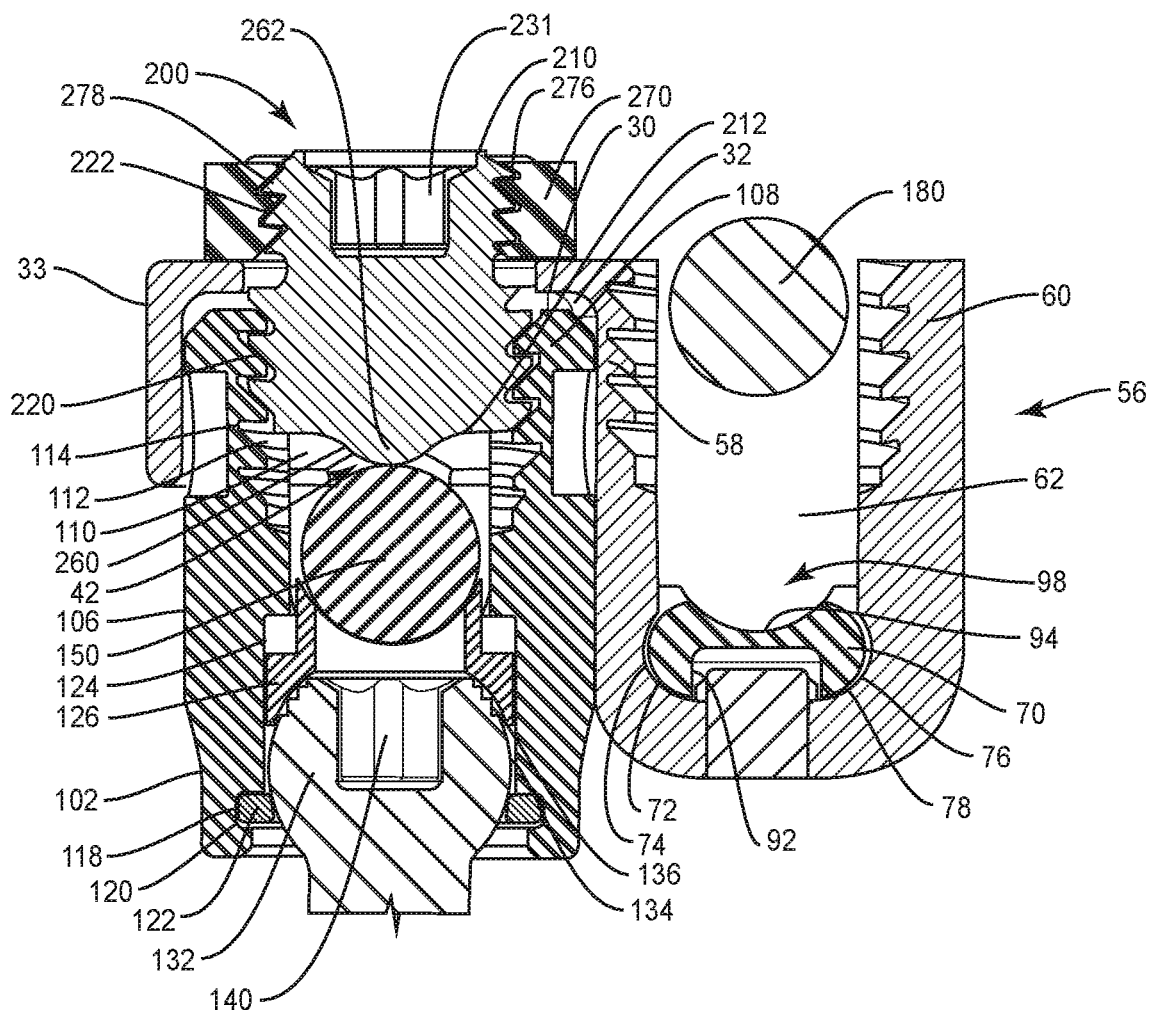
FIG. 9 is a cross section view of the components shown in FIG. 8.
Figure 10:
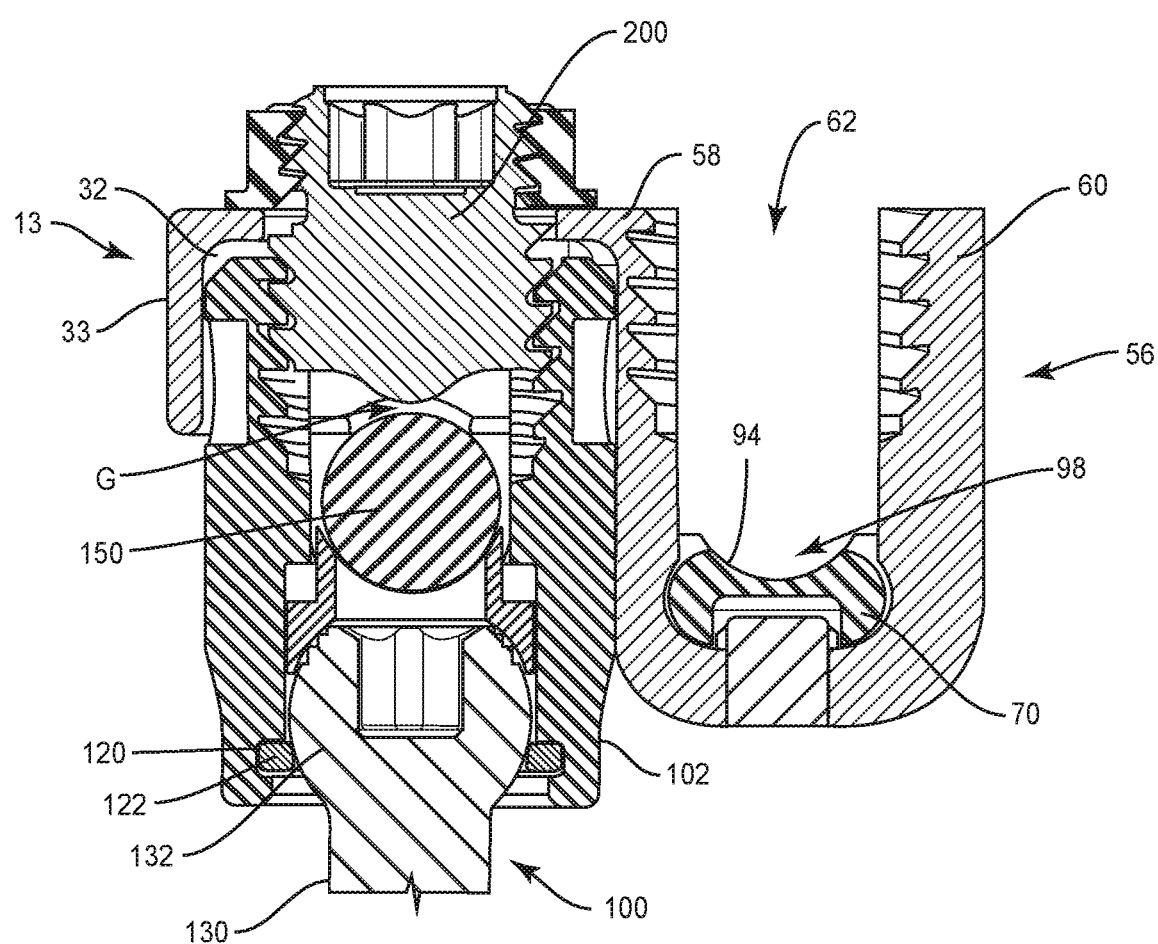
FIG. 10 is a cross section view of components of one embodiment of a system in accordance with the principles of the present disclosure.

Arms 58, 60 are configured to support relative movement of a part, such as, for example, a saddle 70, as described herein. Arm 58 includes a surface 72 that defines a track 74 adjacent arm 58, as shown in FIGS. 8-10. Arm 60 includes a surface 76 that defines a track 78 adjacent arm 60. Tracks 74, 78 are configured to facilitate translation of saddle 70 relative to receiver 56, as described herein. Arms 58, 60 are configured to guide saddle 70 along tracks 74, 78 relative to receiver 56. Receiver 56 includes a surface that defines an arcuate portion 80 configured for disposal of at least a portion of rod 180, which may be positioned with receiver 56.

Saddle 70 extends between an end 82 and an end 84. Saddle 70 includes a surface 86 defining a wall 88 and a wall 90. Walls 88, 90 are configured to fit within the outer profile and/or perimeter of receiver 56. In some embodiments, saddle 70 fits within the outer profile and/or perimeter of receiver 56. Saddle 70 includes a surface 92 configured for slidable engagement with tracks 74, 78. Surface 92 extends between ends 82, 84 and is configured for slidable engagement with receiver 56 along an arcuate pathway of the components. Saddle 70 includes a surface 94 configured to engage at least a portion of rod 180 and is moveable relative to receiver 56 in a plane, such as, for example, a sagittal plane of a body and/or vertebrae and/or in an arcuate path. Surface 94 defines a concave surface that defines a portion of an implant cavity 98 configured for disposal of rod 180. Passageway 62 includes cavity 98.

Receiver 56 defines an axis X5 oriented transverse to axis X2. Saddle 70 is configured to receive and movably support rod 180 such that rod 180 can translate axially, rotate and/or pivot relative to receiver 56 along and about axis X5 prior to fixation with saddle 70. In some embodiments, rod 180 may be disposed within passageway 62 for relative movement in orientations relative to axis X5, such as, for example, transverse, perpendicular and/or other angular orientations such as acute or obtuse, co-axial and/or may be offset or staggered. In some embodiments, axis X5 may be disposed at angular orientations relative to axis X2, such as, for example, acute or obtuse.

In some embodiments, saddle 70 may be elastic and pliable in a configuration to react to forces applied and/or force changes, such as, for example, positioning treatment, patient growth, trauma and degeneration, and/or component creep, deformation, damage and degeneration, to maintain the applied force transmitted from an implant positioned in passageway 62 substantially constant. In some embodiments, saddle 70 can facilitate maintenance of a holding force on a spinal rod positioned in passageway 62 to maintain the holding force relatively constant despite growth and changes.

Saddle 70 translates relative to receiver 56 via relative slidable translation along tracks 74, 78 such that saddle 70 is rotatable relative to receiver 56 in a plane, such as, for example, a sagittal plane of a body and/or vertebrae. Saddle 70 is rotatable along axis X5 through an angular range. Saddle 70 is pivotable along the arcuate path receiver 56 through passageway 62 relative to axis X2. In some embodiments, saddle 70 is disposed with receiver 56 for relative movement of receiver 56 in orientations relative to axis X5, such as, for example, transverse, perpendicular and/or other angular orientations such as acute or obtuse, co-axial and/or may be offset or staggered. In some embodiments, saddle 70 moves relative to receiver 56 in alternate planes relative to a body, such as, for example, vertical, horizontal, diagonal, transverse, coronal and/or sagittal planes of a body. In some embodiments, saddle 70 allows for rod 180 to have a different contour than spinal rod implant 150 to facilitate positioning, as shown in FIG. 11.

Fastener 100 includes receiver 102 that extends along and defines an axis X4. Receiver 102 includes a pair of spaced apart arms 106, 108 that define an implant cavity 110 therebetween configured for disposal of existing spinal rod implant 150. Arms 106, 108 each extend parallel to axis X4. In some embodiments, arm 106 and/or arm 108 may be disposed at alternate orientations, relative to axis X4, such as, for example, transverse, perpendicular and/or other angular orientations such as acute or obtuse, coaxial and/or may be offset or staggered. Arms 106, 108 each include an arcuate outer surface extending between a pair of side surfaces.

Cavity 110 is substantially U-shaped. In some embodiments, all or only a portion of cavity 110 may have alternate cross section configurations, such as, for example, closed, V-shaped, W-shaped, oval, oblong triangular, square, polygonal, irregular, uniform, non-uniform, offset, staggered, and/or tapered. Receiver 102 includes an inner surface 112. A portion of surface 112 includes a thread 114. Thread 114 includes a thread form that is configured for engagement with a coupling member, such as, for example, an existing set screw engaged with fastener 100 and existing spinal rod implant 150. The thread form of thread 114 is also engageable with a set screw 200, as described herein, to retain existing spinal rod implant 150 within cavity 110 and connect connector 13 with fastener 100.

In some embodiments, surface 112 may be disposed with the coupling member in alternate fixation configurations, such as, for example, friction fit, pressure fit, locking protrusion/recess, locking keyway and/or adhesive. In some embodiments, all or only a portion of surface 112 may have alternate surface configurations to enhance engagement, such as, for example, rough, arcuate, undulating, mesh, porous, semi-porous, dimpled and/or textured. Receiver 102 defines a groove 120 configured for disposal of a C-shaped ring 122. Ring 122 engages an outer surface of a head 132 of shaft 130 and is disposable with groove 120 to resist and/or prevent axial translation of shaft 130 relative to receiver 102. Surface 118 includes a slot 124 configured to receive a flange of a crown 126, as shown in FIG. 9.

Shaft 130 is configured to penetrate tissue, such as, for example, bone. Head 132 is engageable with receiver 102. Head 132 includes a substantially spherical proximal portion configured for moveable disposal with receiver 102 and crown 126. Head 132 includes a surface 134 that defines a plurality of ridges 136 to improve purchase of head 132 with crown 126. An engagement portion of crown 126 is concave or semi-spherical to accommodate the substantially spherical configuration of head 132 such that head 132 is rotatable relative to receiver 102.

Head 132 includes a socket 140 having a hexalobe geometry configured for disposal of a similarly shaped bit of a tool, such as, for example, a driver (not shown) to engage the driver with head 132 to rotate shaft 130. Socket 140 is in communication with cavity 110 such that a driver may be inserted between arms 106, 108 and translated axially, until the bit of the driver is disposed in socket 140. In some embodiments, socket 140 has a cruciform, phillips, square, hexagonal, polygonal, star cross sectional configuration configured for disposal of a correspondingly shaped portion of a driver.

Set screw 200 extends between an end 210 and an end 212. Set screw 200 includes a mating surface, such as, for example, a thread 220 and a mating surface, such as, for example, a thread 222. Thread 220 is configured for engagement with thread 114 of fastener 100. In some embodiments, thread 220 includes one or a plurality of threads configured for interlocking engagement with thread 114 of receiver 102, as described herein. In some embodiments, thread 220 is continuous along a portion of set screw 200. In some embodiments, thread 220 may include a single thread turn or a plurality of discrete threads. Thread 220 includes an external thread form 230.

Thread 222 is configured for engagement with a locking member, such as, for example, a nut 270 to fix connector 13 with fastener 100, as described herein. In some embodiments, thread 222 includes one or a plurality of threads configured for interlocking engagement with nut 270, as described herein. In some embodiments, thread 222 is continuous along a portion of setscrew 200. In some embodiments, thread 222 may include a single thread turn or a plurality of discrete threads. Thread 222 includes an external thread form 232. In some embodiments, thread 220 includes a buttress thread that resists and/or prevents pull out from fastener 100. In some embodiments, thread 222 includes a buttress thread that resists and/or prevents pull out from nut 270. In some embodiments, thread 220 is different relative to thread 222, and/or thread 220 defines a thread form that is different relative to a thread form defined by thread 222.

In some embodiments, set screw 200 includes a cavity 231 having a hexagonal cross-section configured to facilitate engagement with a surgical tool or instrument. In some embodiments, cavity 231 may have a cruciform, phillips, square, polygonal or star cross sectional configuration configured for disposal of a correspondingly shaped portion of a surgical tool or instrument.

In some embodiments, end 210 includes a break off portion 224. In some embodiments, portion 224 includes a tool engaging portion configured to engage a surgical tool or instrument (not shown). In some embodiments, portion 224 is frangibly connected to end 210. In some embodiments, portion 224 is fabricated from a fracturing and/or frangible material such that manipulation of portion 224 can fracture and separate portion 224 at a predetermined force and/or torque limit, as described herein. In some embodiments, as force and/or torque is applied to portion 224 and resistance increases, for example, due to fixation of threads 220, 222, as described herein, the predetermined torque and force limit is approached.

In some embodiments, portion 224 can fracture and separate at a predetermined force or torque limit. In some embodiments, portion 224 may be fabricated from a homogenous material or heterogeneously fabricated from different materials, and/or alternately formed of a material having a greater degree, characteristic or attribute of plastic deformability, frangible property and/or break away quality to facilitate fracture and separation of portion 224. In some embodiments, portion 224 includes an inner diameter that facilitates a desired breakoff torque.

In some embodiments, end 212 includes a surface 260 that defines a protrusion 262. Protrusion 262 extends perpendicularly from surface 260 for engagement with existing spinal rod implant 150. In some embodiments, protrusion 262 may be disposed at alternate orientations, such as, for example, transverse and/or other angular orientations such as acute or obtuse, coaxial and/or may be offset or staggered.

Protrusion 262 is configured to apply a force to existing spinal rod implant 150 to facilitate connection of connector 13 with fastener 100. In some embodiments, protrusion 262 is configured to extend into cavity 110 such that a gap G is defined between protrusion 262 and existing spinal rod implant 150. Connector 13 applies a force to existing spinal rod implant 150 adjacent recesses 36, 42 to facilitate connection of connector 13 with fastener 100, as shown in FIG. 10.

Nut 270 includes a tool engaging surface 272 configured to engage a surgical tool or instrument (not shown), as described herein. In some embodiments, surface 272 includes a hexagonal cross-section to facilitate engagement with a surgical tool or instrument. In some embodiments, surface 272 may have alternative cross-sections, such as, for example, rectangular, polygonal, hexalobe, oval, or irregular. Nut 270 includes a surface 274 that defines a cavity 276. Surface 274 includes a thread form 278. Thread form 278 is configured for engagement with thread 222, as described herein, to fix connector 13 with fastener 100 and existing spinal rod implant 150. In some embodiments, surface 272 may be disposed with set screw 200 in alternate fixation configurations, such as, for example, friction fit, pressure fit, locking protrusion/recess, locking keyway and/or adhesive. In some embodiments, all or only a portion of surface 272 may have alternate surface configurations to enhance engagement, such as, for example, rough, arcuate, undulating, mesh, porous, semi-porous, dimpled and/or textured. In some embodiments, nut 270 includes a circumferential flange 280 that applies force and facilitates fixation of connector 13 with fastener 100. In some embodiments, nut 270 includes a break off portion or head 282, similar to that described herein.

Nut 270 is engageable with set screw 200, which is engageable with receiver 102 to fix connector 13 with fastener 100 to revise, repair and/or extend existing spinal rod implant 150. For example, thread 220 is engaged with thread 114. Connector 13 is translated over receiver 102 such that sleeve 33 captures receiver 102. Nut 270 is engaged with thread 222 to fix connector 13 with fastener 100, as described herein. Nut 270 is configured to clamp connector 13 to fastener 100 via set screw 200. Nut 270 causes connector 13 and surface 26 to apply a force to fastener 100 and existing spinal rod implant 150 to fix connector 13 with fastener 100 to revise, repair and/or extend existing spinal rod implant 150. The force is distributed between set screw 200 and surfaces 36, 42, as described herein.

In some embodiments, spinal implant system 10 can include one or a plurality of connectors 13 such as those described herein, which may be employed with a single vertebral level or a plurality of vertebral levels. In some embodiments, one or more connectors 13 may be engaged with vertebrae in various orientations, such as, for example, series, parallel, offset, staggered and/or alternate vertebral levels. In some embodiments, one or more connectors 13 may be employed with multi-axial screws, sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, is employed with a surgical procedure, such as, for example, a surgical treatment of an applicable condition or injury of an affected section of a spinal column and adjacent areas within a body. In some embodiments, spinal implant system 10 includes connector 13, as described herein, which can be employed in a surgical treatment such as a revision surgery to strengthen, revise, repair and/or extend an existing spinal construct. In some embodiments, spinal implant system 10 includes connector 13 employed in a revision surgery to connect with an existing spinal construct and strengthen the existing spinal construct to span one or more spinal levels. In some embodiments, the existing spinal construct may include one or more implants connected or fixed with tissue in a prior or different surgical procedure, separate in time and/or over a duration of time in the same surgical procedure. In some embodiments, during a surgical treatment, spinal implant system 10 may be completely or partially revised, removed or replaced.

Figure 12:
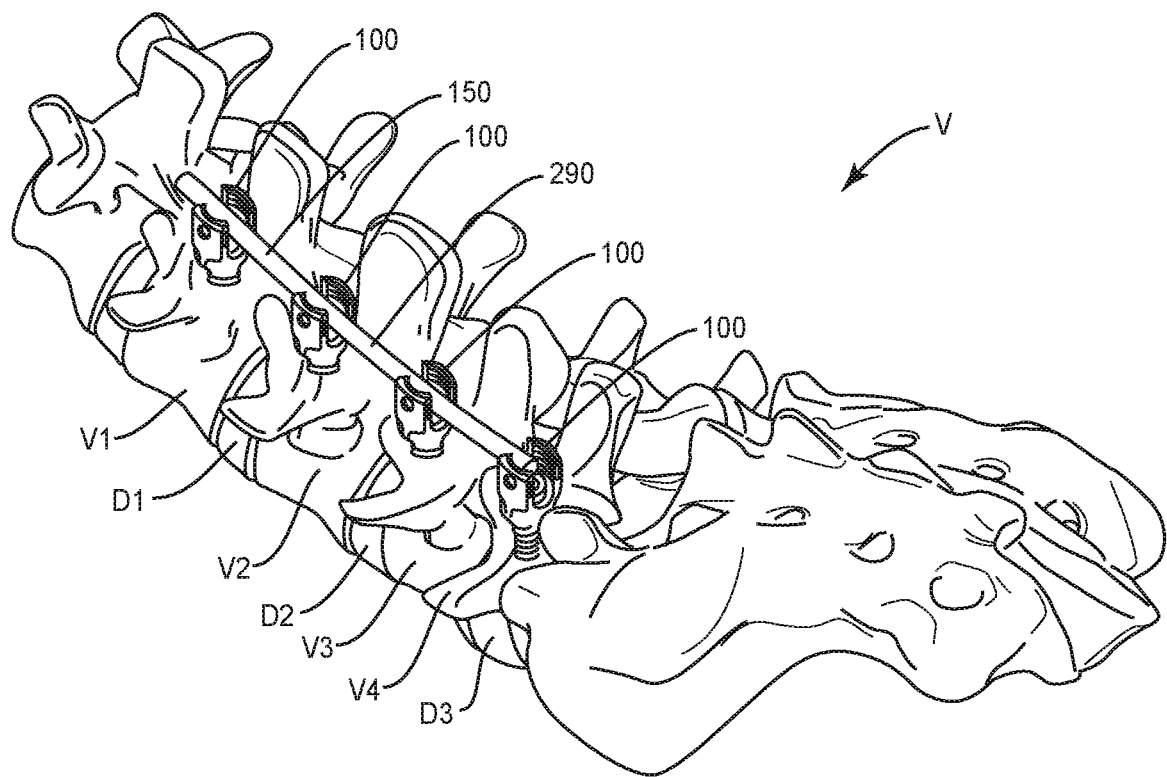
FIG. 12 is a perspective view of components of one embodiment of a system in accordance with the principles of the present disclosure disposed with vertebrae.
Figure 13:
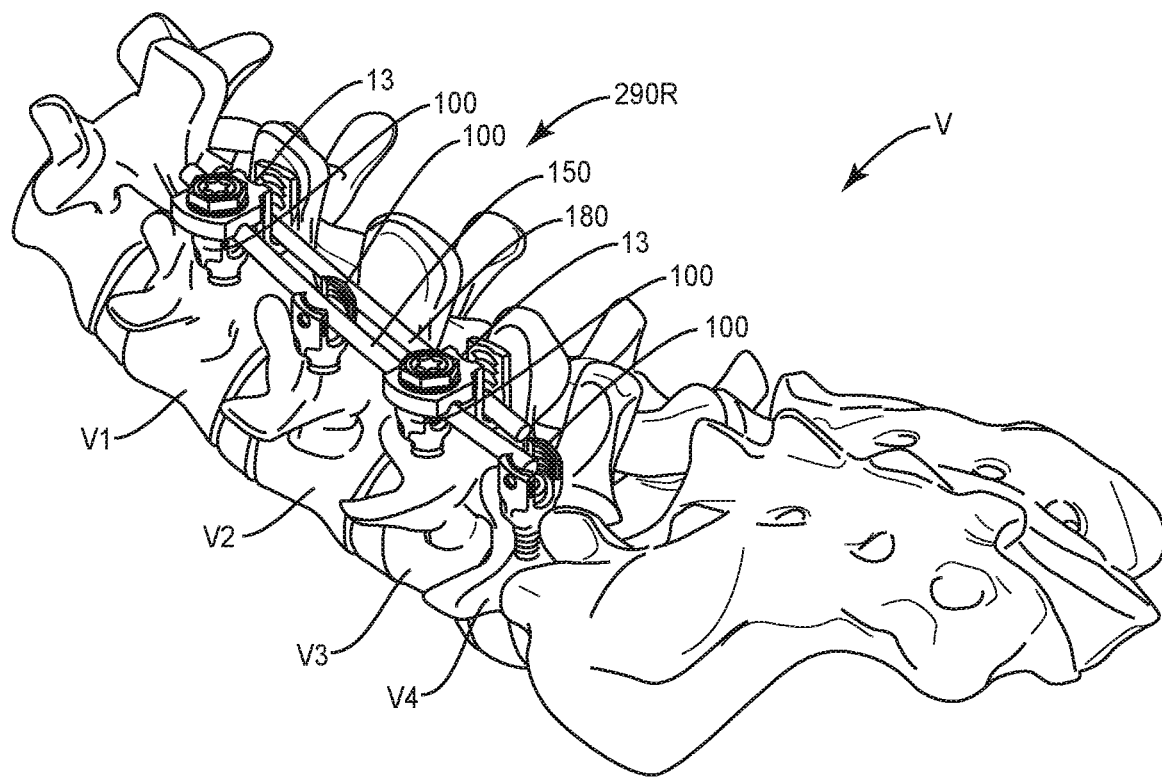
FIG. 13 is a perspective view of components of one embodiment of a system in accordance with the principles of the present disclosure disposed with vertebrae.
Figure 14:
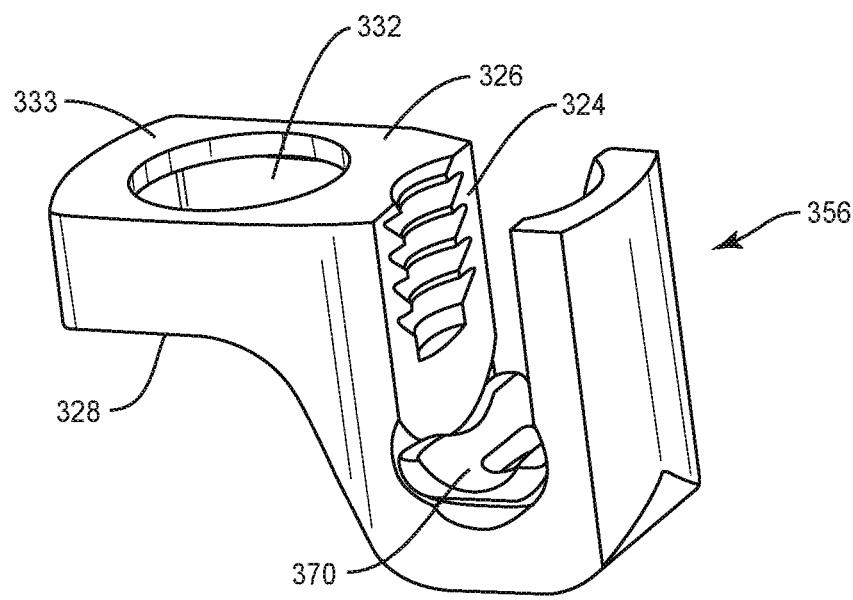
FIG. 14 is a perspective view of components of one embodiment of a system in accordance with the principles of the present disclosure.
Figure 15:
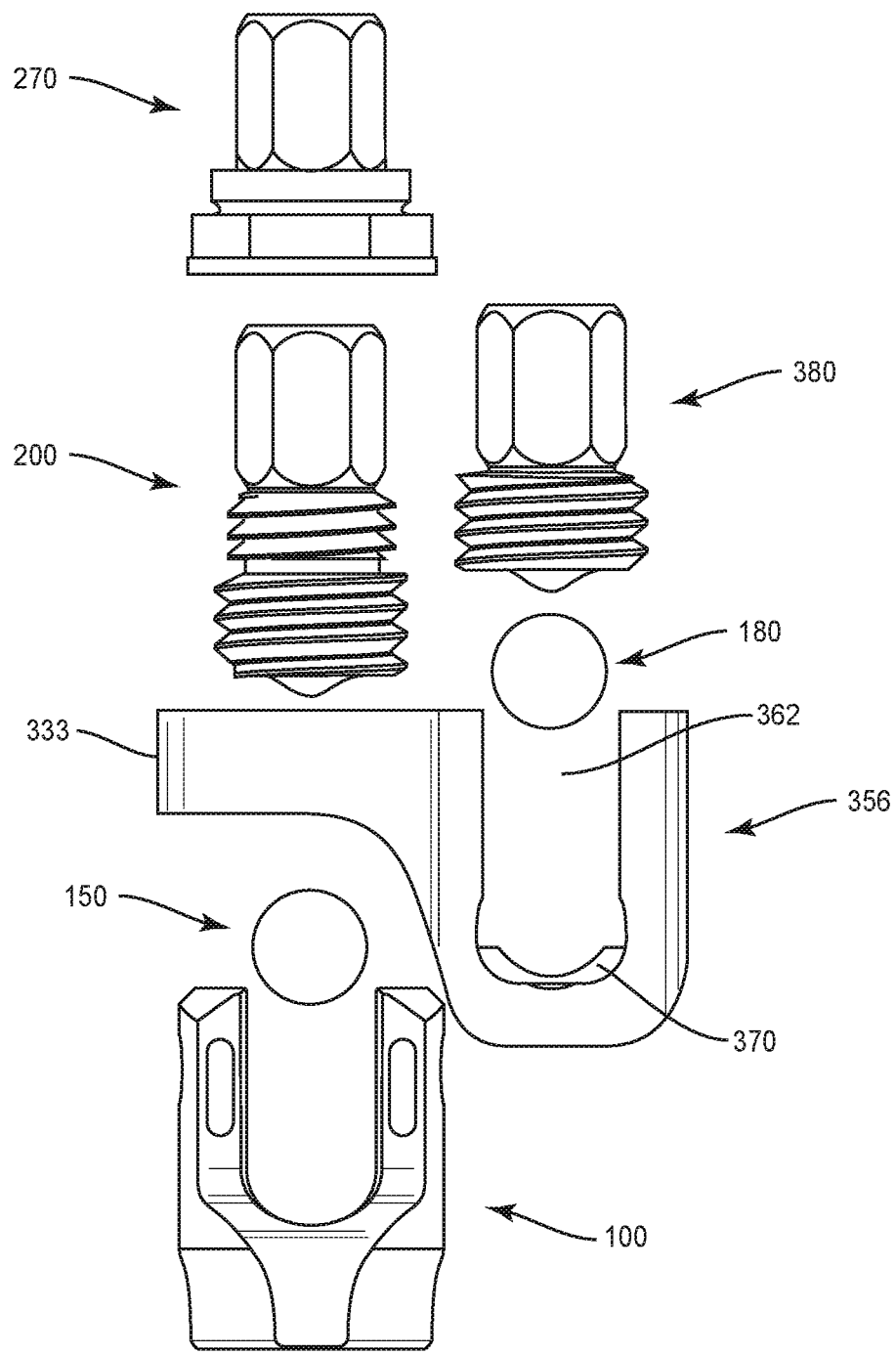
FIG. 15 is a side view of components of one embodiment of a system in accordance with the principles of the present disclosure with parts separated.
Figure 16:
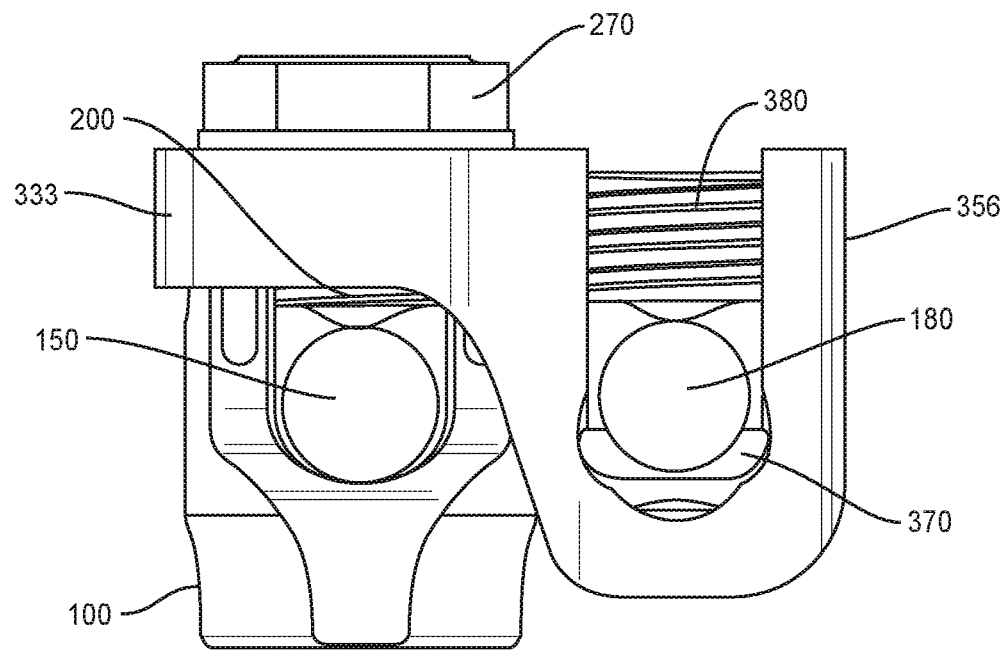
FIG. 16 is a side view of the components shown in FIG. 15.
Figure 17:
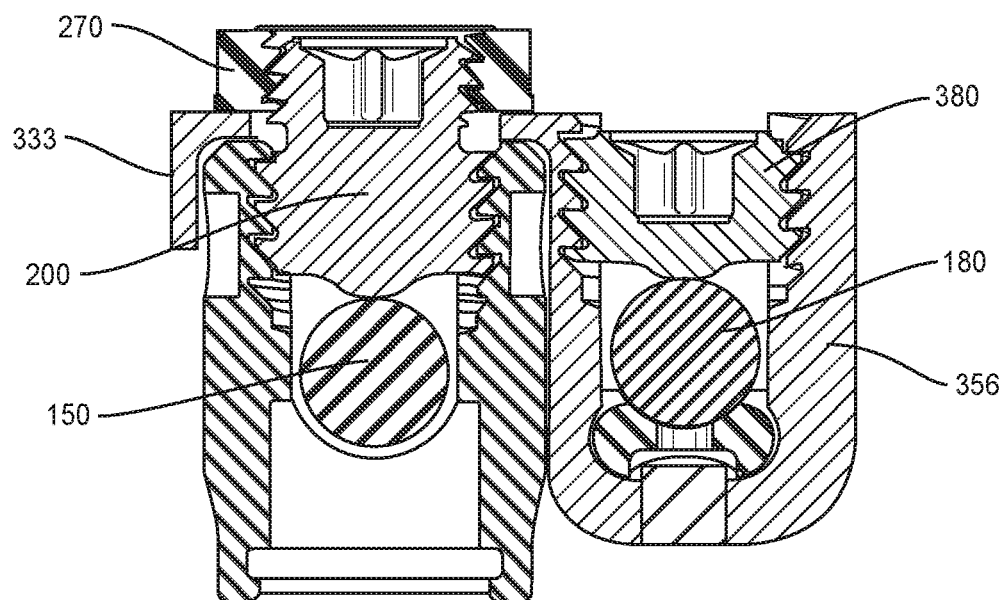
FIG. 17 is a cross section view of components of one embodiment of a system in accordance with the principles of the present disclosure.

For example, a surgical treatment may include adding strength and support to an existing spinal construct 290 that includes fastener 100 and existing spinal rod implant 150, as shown in FIG. 12, implanted with vertebrae V in a prior surgical procedure and spans one or more intervertebral discs. In the prior surgical procedure, existing spinal rod implant 150 is implanted to structurally fuse adjacent vertebrae V1, V2, V3, V4 with existing spinal construct 290, which includes fasteners 100 and existing spinal rod implant 150, to span intervertebral discs D1, D2, D3. In one example, the surgical procedure requires utilization of multiple rods, such as, for example, existing spinal rod implant 150 and rod 180, as shown in FIG. 13. In some embodiments, multiple rods are required for a high load demand, such as, for example, a pedicle subtraction osteotomy, a lumbar fixation, a heavier patient and/or a revision surgery subsequent or different to the prior surgical procedure. In some embodiments, the treatment includes connector 13 employed in a revision surgery to connect with spinal rod 150 to form a revised spinal construct 290R that strengthens spinal construct 290 along spinal levels V1-V4, as described herein. In some embodiments, this configuration avoids disruption and tissue damage of the area of the prior surgical procedure, and reduction in healing and treatment duration.

In connection with the surgical procedure, to treat a selected section of vertebrae V, including vertebrae V1, V2, V3, V4 as shown in FIGS. 12 and 13, a medical practitioner obtains access to a surgical site including vertebrae V in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access an existing spinal construct 290 including implanted fastener 100 and implanted existing spinal rod implant 150. The surgical pathway is utilized for implantation of components of spinal implant system 10. A preparation instrument (not shown) can be employed to prepare tissue surfaces of vertebrae V, as well as for aspiration and irrigation of a surgical region.

A set screw (not shown) that connected faster 100 and existing spinal rod implant 150 is removed from fastener 100. Set screw 200 is connected with a surgical instrument and delivered along the surgical pathway to engage fastener 100. Set screw 200 is rotated such that thread 220 engages thread 114 to fix set screw 200 with fastener 100. Connector 13 is translated over receiver 102 such that arms 106, 108 are captured by sleeve 33 within cavity 32. Connector 13 is moveable relative to fastener 100 and existing spinal rod implant 150 for orientation.

Nut 270 is translated into engagement with set screw 200 such that thread 222 engages thread form 278. Translation of nut 270 clamps connector 13 between existing spinal rod implant 150 and nut 270. The force applied to existing spinal rod implant 150 is distributed between set screw 200 and recesses 36, 42.

Spinal rod 180 is delivered along the surgical pathway and is disposed with passageway 62 and saddle 70. Saddle 70 receives and movably supports spinal rod 180 such that spinal rod 180 is movable within passageway 62. Tracks 74, 76 facilitate translation of saddle 70 relative to receiver 56 for adjustment of rod 180 therein. In some embodiments, saddle 70 is selectively translatable along tracks 74, 76 and the arcuate path of saddle 70 relative to receiver 56 in the sagittal plane to accommodate sagittal anatomical differences.

Spinal rod 180 is fixed with receiver 56 with a set screw (not shown). The set screw is engaged with a surgical instrument, such as, for example, a driver (not shown), which advances the set screw into engagement with arms 58, 60 in a locking orientation, as described herein. The driver engages the set screw to fix spinal rod 180 with receiver 56 and for attachment of spinal rod 180 with vertebrae V.

Connector 13 and rod 180 are manipulated to dispose rod 180 in a position to support and strengthen existing spinal construct 290 to form a revised spinal construct 290R, as shown in FIG. 13. Rod 180 is manipulated into a parallel orientation relative to spinal rod 150 in at least one pair of planes for connection with connectors 13 and fasteners 100, which are fastened with vertebrae V. Spinal construct 290R strengthens existing spinal construct 290 along vertebrae V1-V4, as shown in FIG. 13, without disruption of existing spinal construct 290. Spinal construct 290R is configured to structurally fuse adjacent vertebrae V1-V4. In some embodiments, rod 180 is configured to add support and strength to spinal implant system 10 along vertebrae V. In some embodiments, spinal construct 290R is adjustable to selectively span one or more vertebrae.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, robotics, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 14-17, spinal implant system 10, similar to the systems and methods described herein, includes a spinal construct that includes a connector 313, similar to connector 13 described herein. The spinal construct can be employed with an existing spinal construct, similar to that described herein, for example, spinal construct 290 including fastener 100 and existing spinal rod implant 150, as described herein.

Connector 313 includes a wall 324 that includes a sleeve 333, similar to sleeve 33 described herein. Sleeve 333 extends between a surface 326 and a surface 328. In some embodiments, surfaces 326, 328 include a planar configuration. Sleeve 333 defines a cavity 332, similar to cavity 32 described herein. Connector 313 includes a receiver 356, similar to receiver 56 described herein. Receiver 356 defines a passageway 362, similar to passageway 62 described herein. Receiver 356 includes a saddle 370, similar to saddle 70 described herein. Receiver 356 is configured for disposal of rod 180, as described herein.

Nut 270 is engageable with set screw 200 to fix connector 313 with fastener 100 to revise, repair and/or extend existing spinal rod implant 150, as described herein. Nut 270 is configured to clamp connector 313 to fastener 100 via set screw 200. Set screw 200 engages fastener 100 for connection with connector 313 and surface 260 applies a force to existing spinal rod implant 150 to fix connector 313 with fastener 100 to revise, repair and/or extend existing spinal rod implant 150.

In use, a set screw (not shown) that connected fastener 100 and existing spinal rod implant 150 is removed from fastener 100. Set screw 200 is connected with a surgical instrument (not shown) and delivered along a surgical pathway to engage fastener 100, as shown in FIG. 18. Set screw 200 is rotated such that thread 220 engages thread 114 to fix set screw 200 with fastener 100. Connector 313 is translated over receiver 102 such that arms 106, 108 are captured by sleeve 333 within cavity 332, as shown in FIG. 19. Connector 313 is moveable relative to fastener 100 and existing spinal rod implant 150 for orientation. Break off portion 224 is removed, as shown in FIG. 20. Nut 270 is translated into engagement with set screw 200 such that thread 222 engages thread form 278, as shown in FIG. 21. Translation of nut 270 clamps connector 313 between existing spinal rod implant 150 and nut 270. Surface 262 applies force to existing spinal rod implant 150.

Figure 24:
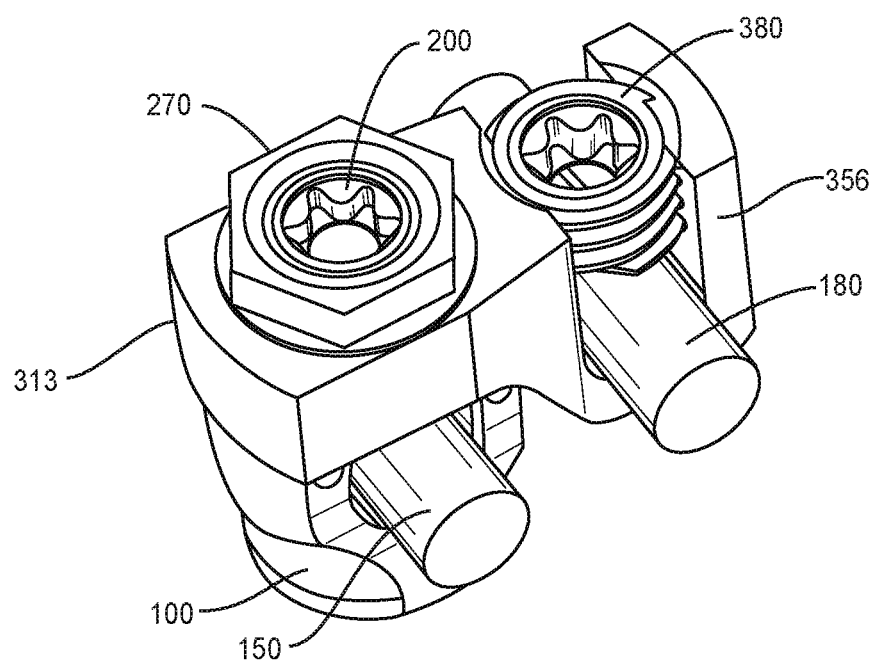
FIG. 24 is a perspective view of components of one embodiment of a system in accordance with the principles of the present disclosure.
Figure 25:
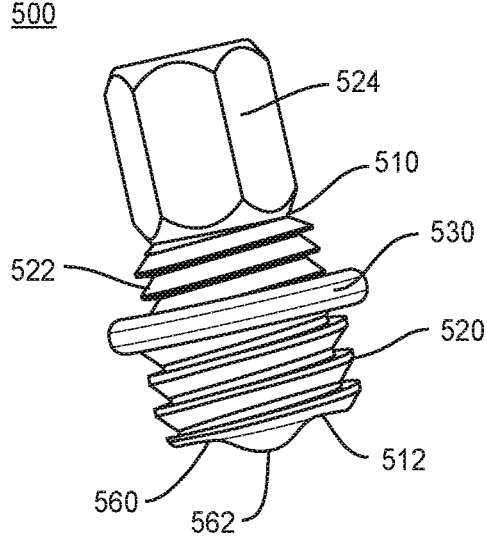
FIG. 25 is a side view of components of one embodiment of a system in accordance with the principles of the present disclosure.
Figure 26:
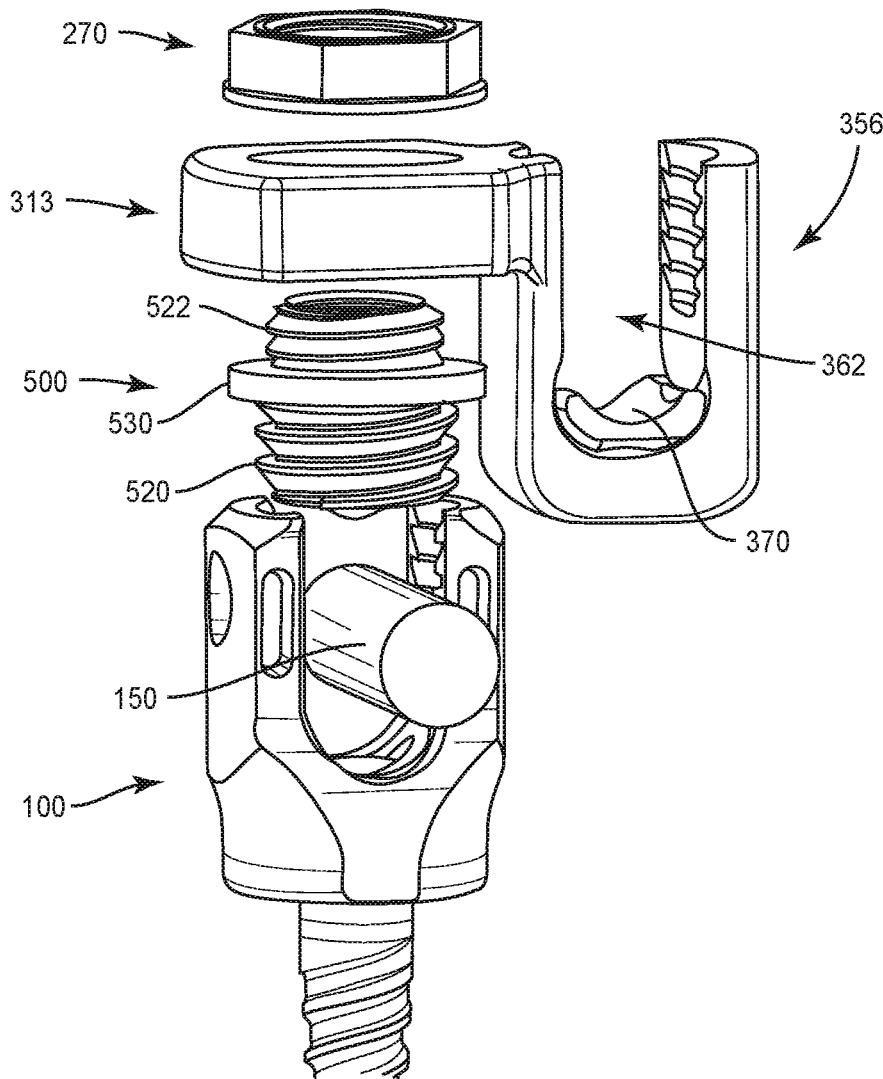
FIG. 26 is a perspective view of components of one embodiment of a system in accordance with the principles of the present disclosure with parts separated.

Spinal rod 180 is delivered along the surgical pathway and is disposed with passageway 362 and saddle 370 from a top loading orientation. Saddle 370 receives and movably supports spinal rod 180 such that spinal rod 180 is movable within passageway 362. Spinal rod 180 is fixed with receiver 356 via a set screw 380, as shown in FIGS. 22-24. Set screw 380 is engaged with a surgical instrument, such as, for example, a driver (not shown), which advances set screw 380 into engagement with receiver 356 in a locking orientation, as described herein. The driver engages set screw 380 to fix spinal rod 180 with receiver 356 and for attachment of spinal rod 180 with vertebrae V.

Connector 313 and rod 180 are manipulated to dispose rod 180 in a position to support, strengthen and/or extend existing spinal construct 290 to form a revised spinal construct, similar to that shown in FIG. 13. Rod 180 is manipulated into a parallel orientation relative to spinal rod 150 for connection with connectors 313 and fasteners 100, which are fastened with vertebrae V. Rod 180 is utilized in conjunction with existing spinal rod implant 150 to add support and strength to spinal implant system 10 along vertebrae V to form the revised spinal construct.

In one embodiment, as shown in FIGS. 25-28, spinal implant system 10, similar to the systems and methods described herein, includes a spinal construct that includes connector 313, as described herein. The spinal construct can be employed with an existing spinal construct, similar to that described herein, for example, spinal construct 290 including faster 100 and existing spinal rod implant 150.

The spinal construct includes a set screw 500 engageable with fastener 100 and connector 313, similar to set screw 200 described herein. Set screw 500 extends between an end 510 and an end 512. Set screw 500 includes a thread 520, similar to thread 220 described herein and a thread 522, similar to thread 222 described herein. Thread 520 is configured for engagement with thread 114. Thread 520 includes an external thread form.

Thread 522 is engageable with nut 270 to fix connector 313 with fastener 100, as described herein. Thread 522 includes an external thread form. End 510 includes a break off portion 524, similar to portion 224 described herein. End 512 includes a surface 560 that defines a protrusion 562, similar to protrusion 62 described herein.

Figure 27:
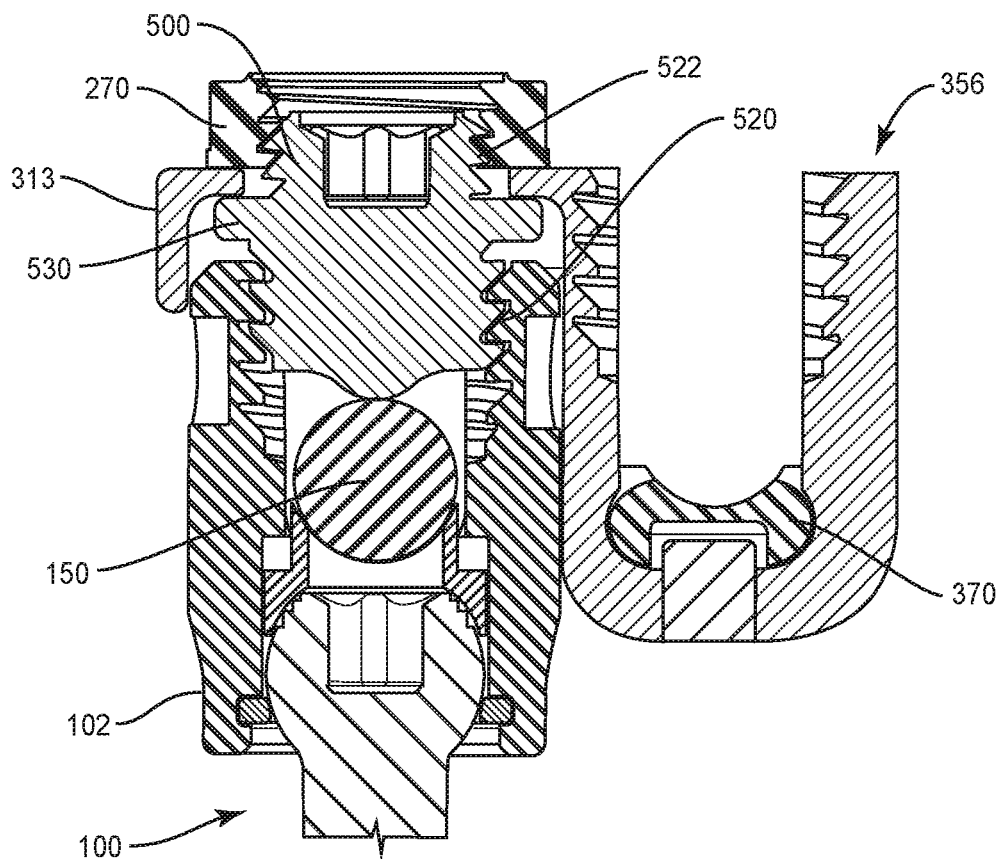
FIG. 27 is a cross section view of the components shown in FIG. 26.
Figure 28:
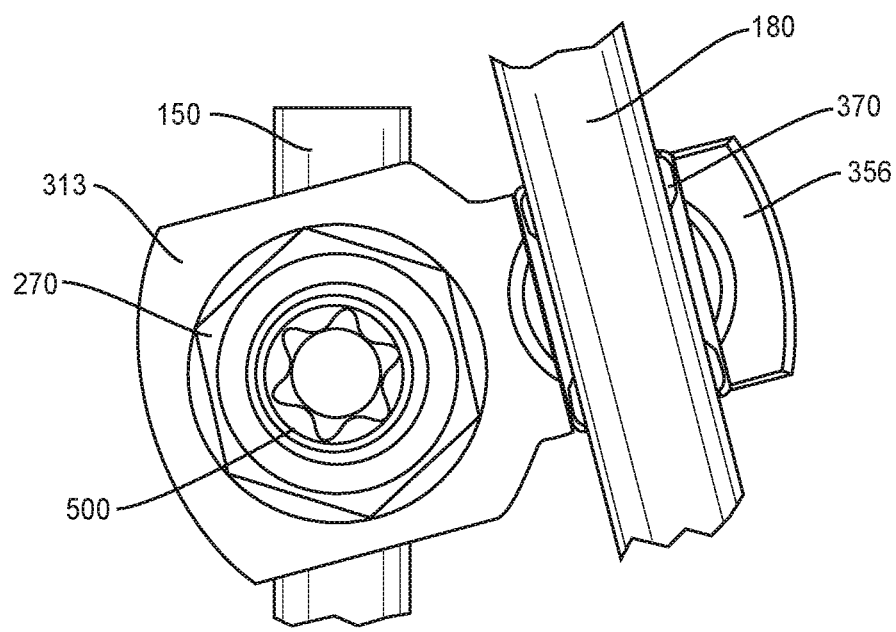
FIG. 28 is a plan view of the components shown in FIG. 27.
Figure 29:
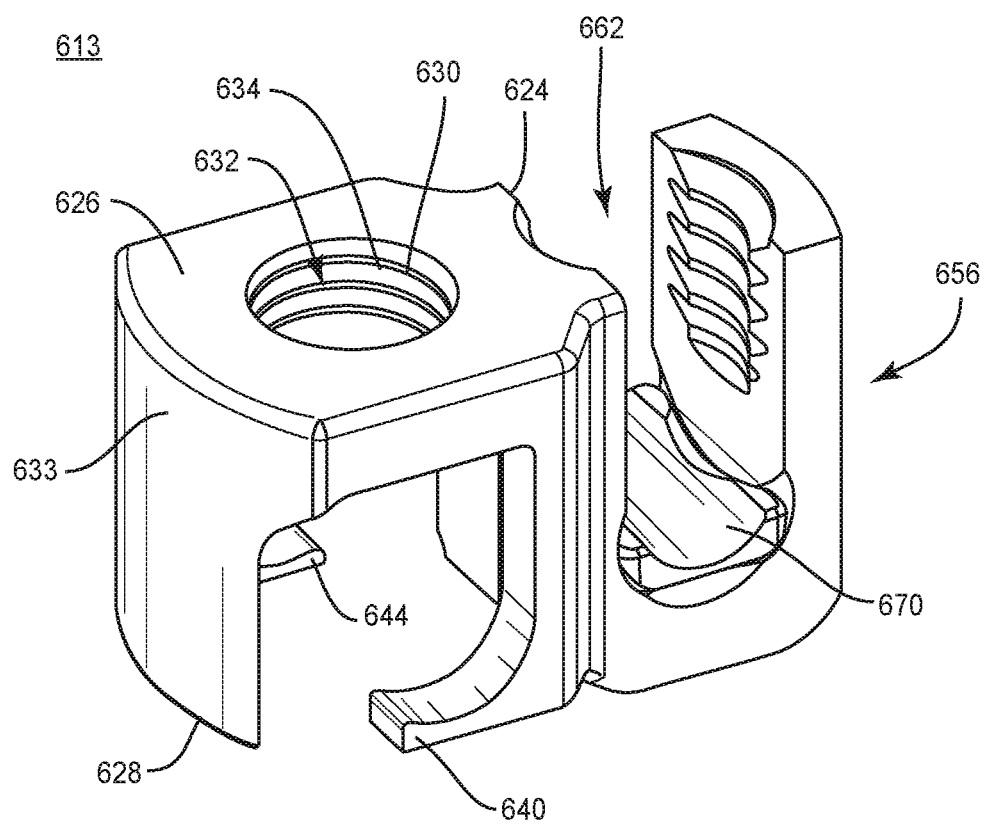
FIG. 29 is a perspective view of components of one embodiment of a system in accordance with the principles of the present disclosure.
Figure 30:
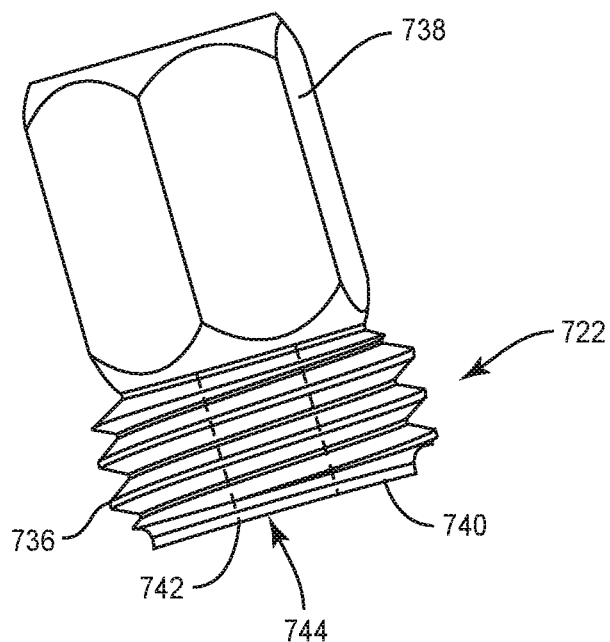
FIG. 30 is a side view of components of one embodiment of a system in accordance with the principles of the present disclosure
Figure 31:
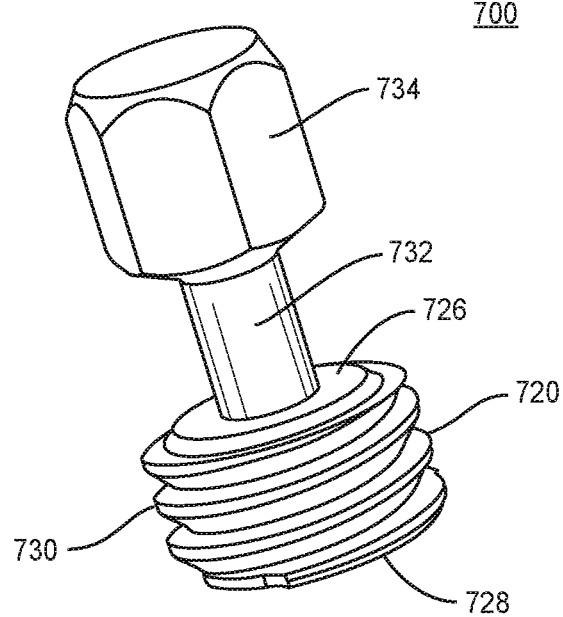
FIG. 31 is a perspective view of components of one embodiment of a system in accordance with the principles of the present disclosure.
Figure 32:
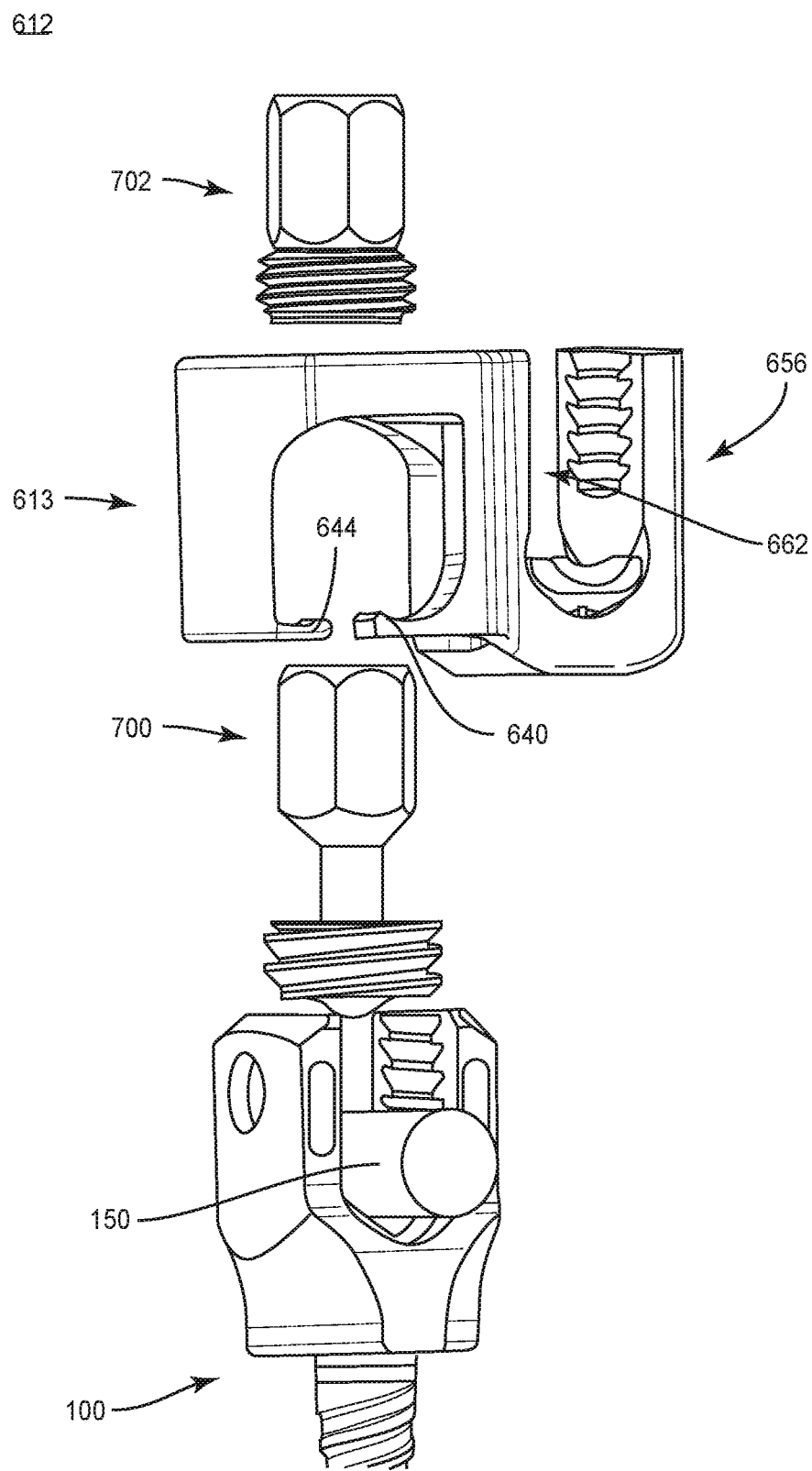
FIG. 32 is a perspective view of components of one embodiment of a system in accordance with the principles of the present disclosure with parts separated.

Set screw 500 includes a protrusion, such as, for example, a circumferential flange 530. Flange 530 is configured for disposal between and to clamp nut 270 and receiver 102, as shown in FIG. 27. Flange 530 distributes a load from connector 313 to receiver 102. In some embodiments, connector 313 is rotatable on and relative to flange 530 to facilitate orientation of spinal rod 180 relative to rod 150 and/or with receiver 356, as shown in FIG. 28.

In one embodiment, as shown in FIGS. 29-38, spinal implant system 10, similar to the systems and methods described herein, includes a spinal construct that includes a connector 613, similar to connector 13 described herein. The spinal construct can be employed with an existing spinal construct, similar to that described herein, for example, spinal construct 290 including faster 100 and existing spinal rod implant 150.

Connector 613 includes a wall 624 that includes a sleeve 633, similar to sleeve 33 described herein. Sleeve 633 extends between a surface 626 and a surface 628. Sleeve 633 includes a surface 630 that defines a cavity 632. Surface 630 includes a thread form 634. Thread form 634 is configured for engagement with a thread 722 of a set screw 702, as described herein, to fix connector 613 with fastener 100 and existing spinal rod implant 150. In some embodiments, surface 630 may be disposed with set screw 702 in alternate fixation configurations, such as, for example, friction fit, pressure fit, locking protrusion/recess, locking keyway and/ or adhesive. In some embodiments, all or only a portion of surface 630 may have alternate surface configurations to enhance engagement, such as, for example, rough, arcuate, undulating, mesh, porous, semi-porous, dimpled and/or textured.

Figure 34:
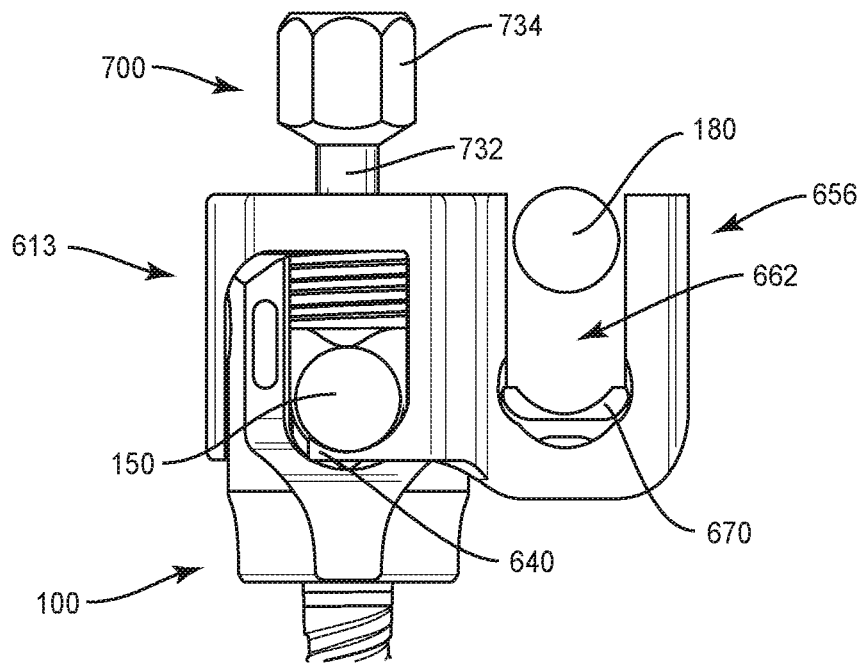
FIG. 34 is a side view of components of one embodiment of a system in accordance with the principles of the present disclosure.

Sleeve 633 includes one or more projections, such as, for example, hooks 640, 644. Hooks 640, 644 are configured to capture existing spinal rod implant 150, as shown in FIG. 34. In some embodiments, hook 640 and/or hook 644 include an arcuate configuration. In some embodiments, hook 640 and/or hook 644 are configured to conform to the shape of existing spinal rod implant 150, as described herein. Hook 644 is disposed in alignment with hook 640 to facilitate disposal of existing spinal rod implant 150 with connector 613.

Connector 613 includes a receiver 656, similar to receiver 56 described herein. Receiver 656 defines a passageway 662, similar to passageway 62 described herein. Receiver 656 includes a saddle 670, similar to saddle 70 described herein. Receiver 656 is configured for disposal of rod 180, as described herein.

Spinal construct 612 includes a set screw 700 and set screw 702, similar to the set screws described herein. Set screw 700 includes a mating surface, such as, for example, a thread 720. Thread 720 is configured for engagement with thread 114, as described herein. Thread 720 extends between a surface 726 and a surface 728. Thread 720 includes an external thread form 730.

A stem 732 extends from surface 726. Stem 732 extends perpendicular to surface 726. In some embodiments, stem 732 may be disposed at alternate orientations relative to surface 726, such as, for example, transverse, and/or other angular orientations such as acute or obtuse, coaxial and/or may be offset or staggered. Stem 732 is disposable with an interior cavity of set screw 702, as described herein. Stem 732 guides set screw 702 into engagement with connector 613. In some embodiments, stem 732 is configured to facilitate removal of set screw 702. In some embodiments, stem 732 includes a break off portion 734, similar to the break off portions described herein. In some embodiments, portion 734 includes a tool engaging portion configured to engage a surgical tool or instrument (not shown).

Figure 38:
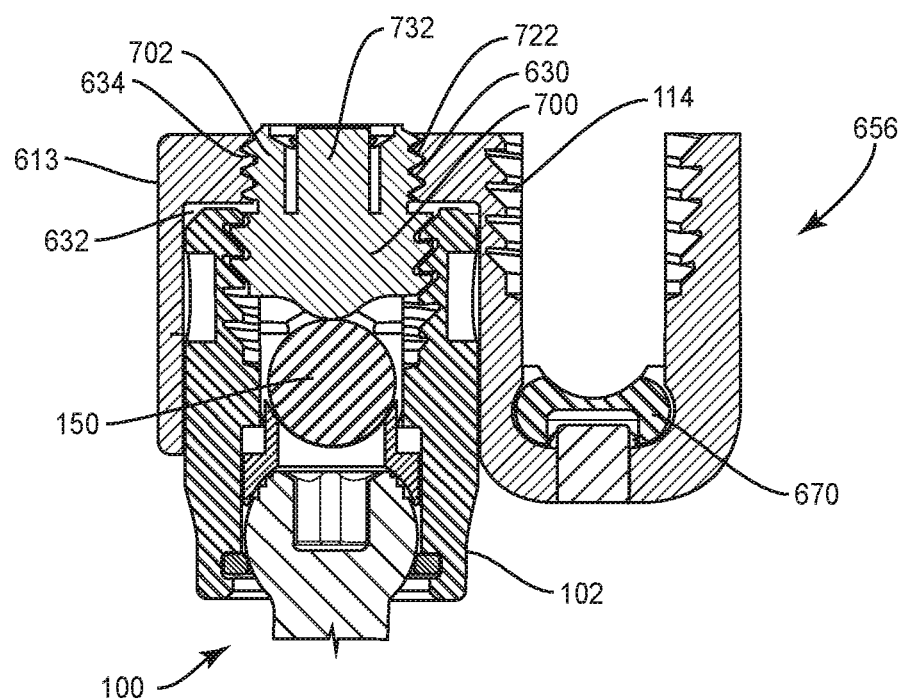
FIG. 38 is a cross section view of the components shown in FIG. 36.

Set screw 702 includes a mating surface, such as, for example, a thread 722. Thread 722 is configured for engagement with connector 613 to fix connector 613 with fastener 100, as shown in FIG. 38. Thread 722 includes an external thread form 736. In some embodiments, set screw 702 includes a break off portion 738, similar to the break off portions described herein. In some embodiments, portion 738 includes a tool engaging portion configured to engage a surgical tool or instrument (not shown). Set screw 702 includes a bearing surface 740 engageable with surface 726. Set screw 702 includes a surface 742 that defines a cavity 744. Cavity 744 is configured for disposal of stem 732.

Figure 33:
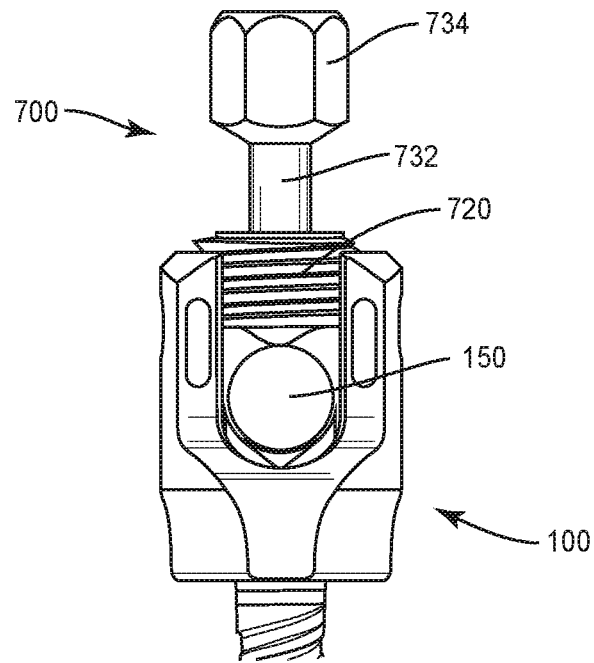
FIG. 33 is a side view of components of one embodiment of a system in accordance with the principles of the present disclosure.
Figure 35:
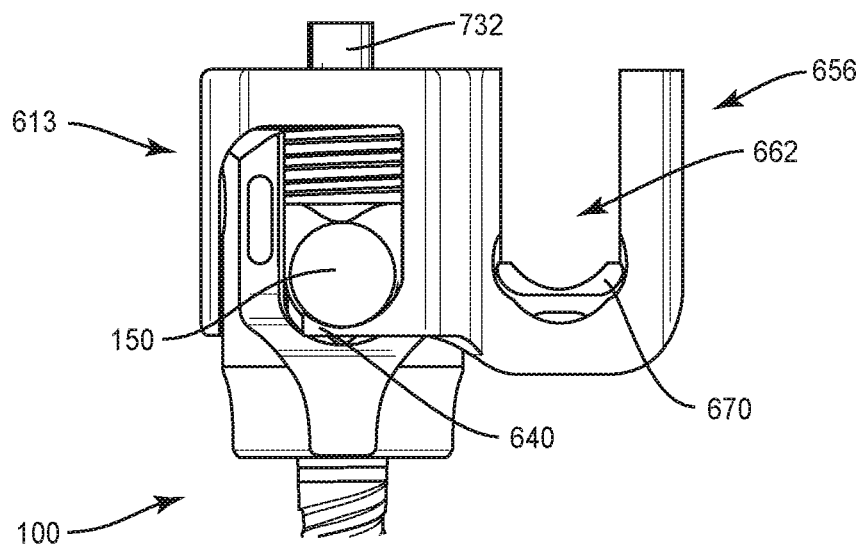
FIG. 35 is a side view of components of one embodiment of a system in accordance with the principles of the present disclosure.
Figure 36:
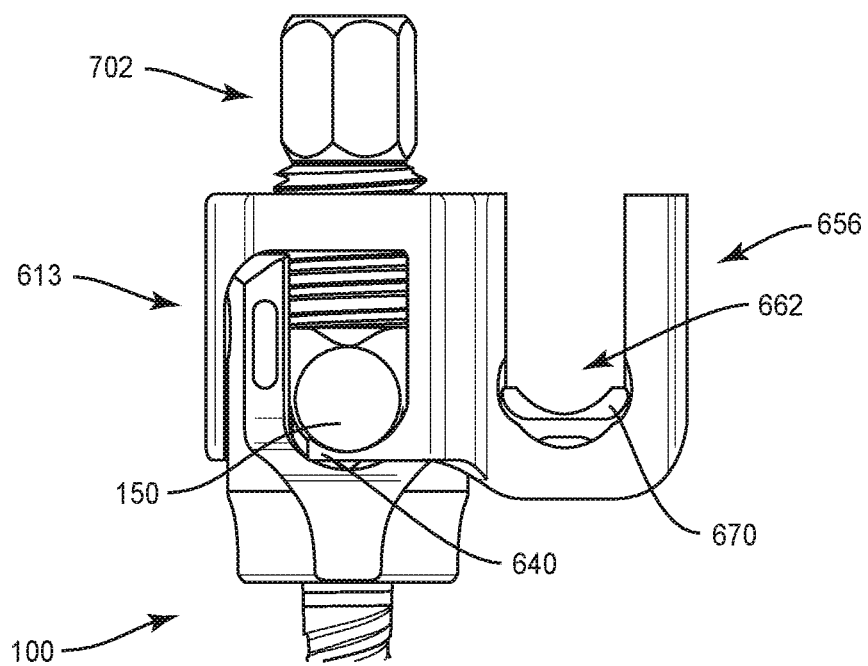
FIG. 36 is a side view of components of one embodiment of a system in accordance with the principles of the present disclosure.
Figure 37:
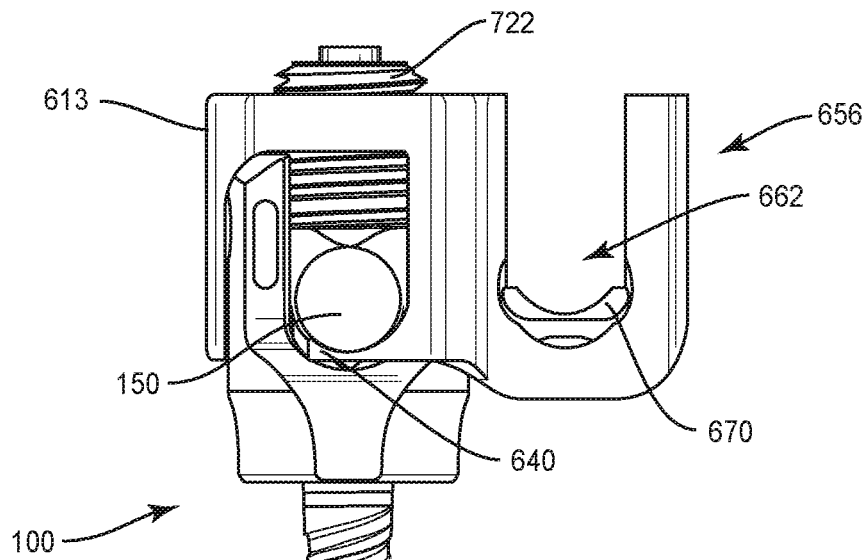
FIG. 37 is a side view of the components shown in FIG. 36.

In use, similar to the systems and methods described herein, a set screw (not shown) that connected fastener 100 and existing spinal rod implant 150 is removed and set screw 700 is delivered along a surgical pathway to engage fastener 100. Thread 720 engages thread 114 to fix set screw 700 with fastener 100. Set screw 700 applies a force to existing spinal rod implant 150 for fixation with fastener 100, as shown in FIG. 33. Connector 613 translates over receiver 102 such that arms 106, 108 are captured by sleeve 633 and manipulated/rotated to capture existing spinal rod implant 150 with hooks 640, 644, as shown in FIG. 34. Portion 734 is removed from stem 732, similar to break off described herein and as shown in FIG. 35.

Thread 722 engages thread form 634 to translate set screw 702 over stem 732 into engagement with set screw 700. Set screw 702 draws connector 613 upward to drive hooks 640, 644 into engagement with existing spinal rod implant 150. The force applied via set screw 702 is distributed to fix connector 613 with existing spinal rod implant 150 and fastener 100.

Spinal rod 180 is delivered along the surgical pathway and is disposed with passageway 662. Saddle 670 receives and movably supports spinal rod 180 such that spinal rod 180 is movable within passageway 662, similar to that described herein. Spinal rod 180 is fixed with receiver 656 with a set screw (not shown), similar to that described herein. Spinal rod 180 is fixed with receiver 656 for attachment with tissue.

Figure 39:
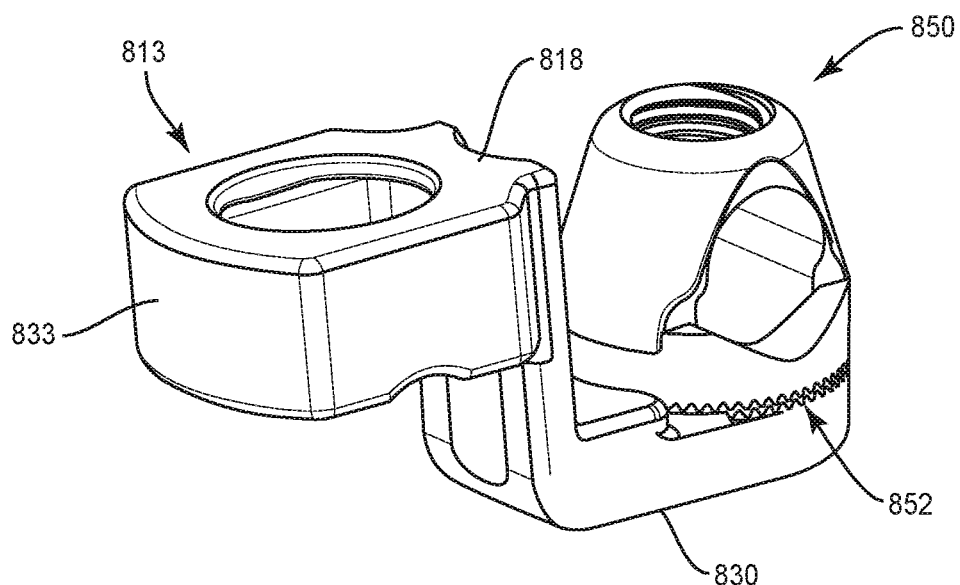
FIG. 39 is a perspective view of components of one embodiment of a system in accordance with the principles of the present disclosure
Figure 40:
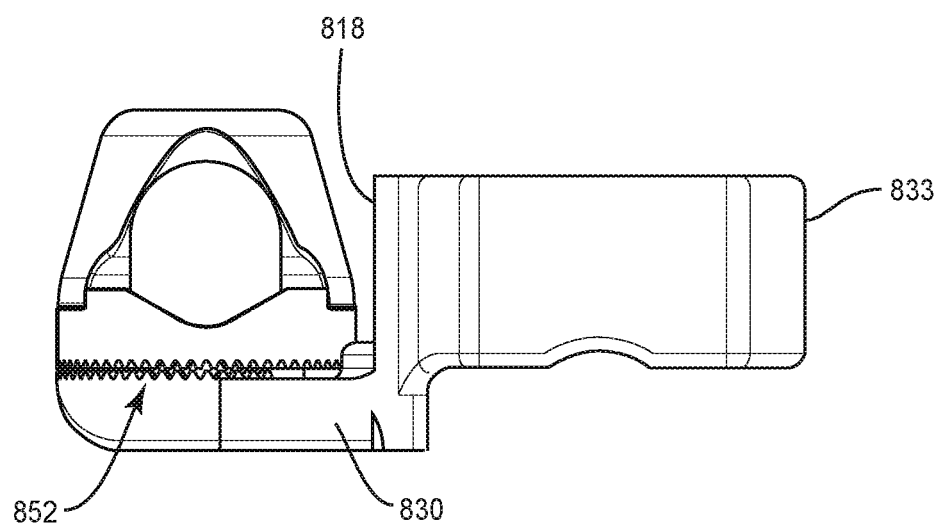
FIG. 40 is a side view of the components shown in FIG. 39.

In one embodiment, as shown in FIGS. 39 and 40, spinal implant system 10, similar to the systems and methods described herein, includes a connector 813, similar to the connectors described herein, which can be employed with an existing spinal construct, similar to that described herein. Connector 813 includes a sleeve 833, similar to sleeve 33 described herein. Sleeve 833 is configured for disposal of receiver 102 of fastener 100, as described herein. Connector 813 includes an extension 830 extending from wall 818.

A body 850 is connected with extension 830. Body 850 is connected with extension 830 via a splined connection 852. Splined connection 852 is configured to facilitate incremental and selective positioning of spinal rod 180 relative to an existing spinal construct via relative movement of the respective spline surfaces, and locking of spinal rod 180 relative to the existing spinal construct via mesh engagement of the respective spline surfaces. Splined connection 852 is moveable between an unlocked and a locked configuration to selectively rotate spinal rod 180 to a selected position relative to the existing spinal construct and/or tissue. Engagement of a set screw, similar to those described herein, with body 850 causes the splined surfaces of splined connection 852 to interlock and fix the selected position of rod 180. In some embodiments, splined connection 852 allows for rotation of rod 180, which may include secondary rod angulation, for example in a coronal orientation or plane, before the set screw is tightened and/or interdigitate when the set screw is tightened to lock a spinal construct.

Figure 41:
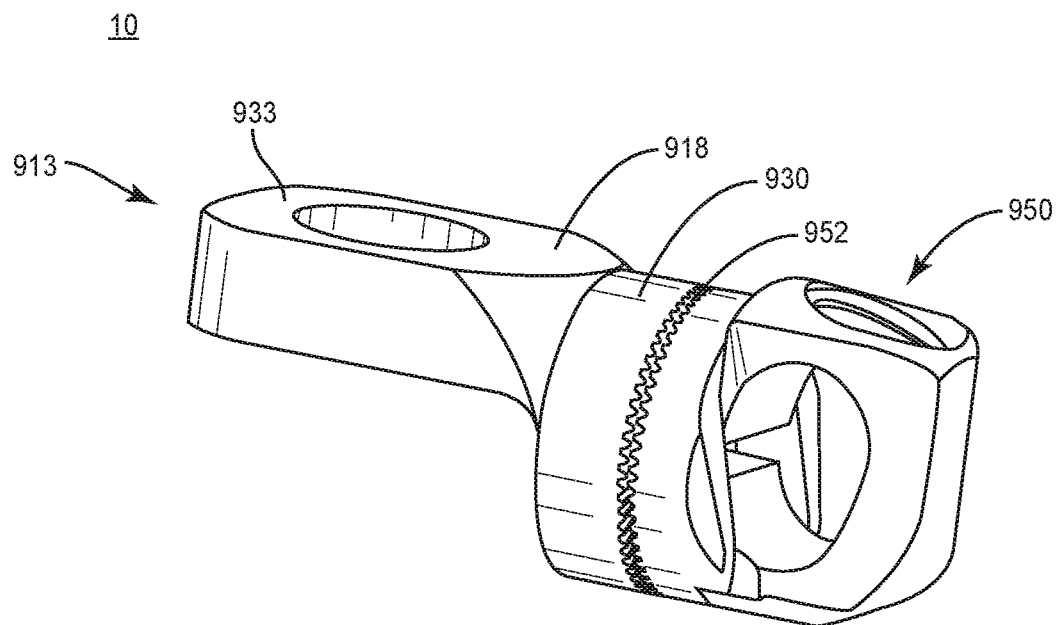
FIG. 41 is a perspective view of components of one embodiment of a system in accordance with the principles of the present disclosure.

In one embodiment, as shown in FIG. 41, spinal implant system 10, similar to the systems and methods described herein, includes a connector 913, similar to the connectors described herein, which can be employed with an existing spinal construct, similar to that described herein. Connector 913 includes a sleeve 933, similar to the sleeves described herein. Sleeve 933 is configured for disposal of receiver 102 of fastener 100, as described herein. Connector 913 includes an extension 930 extending from a wall 918.

A body 950 is connected with extension 930. Body 950 is connected with extension 930 via a splined connection 952. Splined connection 952 is configured to facilitate incremental and selective positioning of spinal rod 180 relative to an existing spinal construct via relative movement of the respective spline surfaces, and locking of spinal rod 180 relative to the existing spinal construct via mesh engagement of the respective spline surfaces. Splined connection 952 is moveable between an unlocked and a locked configuration to selectively rotate spinal rod 180 to a selected position relative to the existing spinal construct and/or tissue. Engagement of a set screw, similar to those described herein, with body 950 causes the splined surfaces of splined connection 952 to interlock and fix the selected position of rod 180. In some embodiments, splined connection 952 allows for rotation of rod 180, which may include secondary rod angulation, for example in a sagittal orientation, before the set screw is tightened and/or interdigitate when the set screw is tightened to lock a spinal construct.

Figure 42:
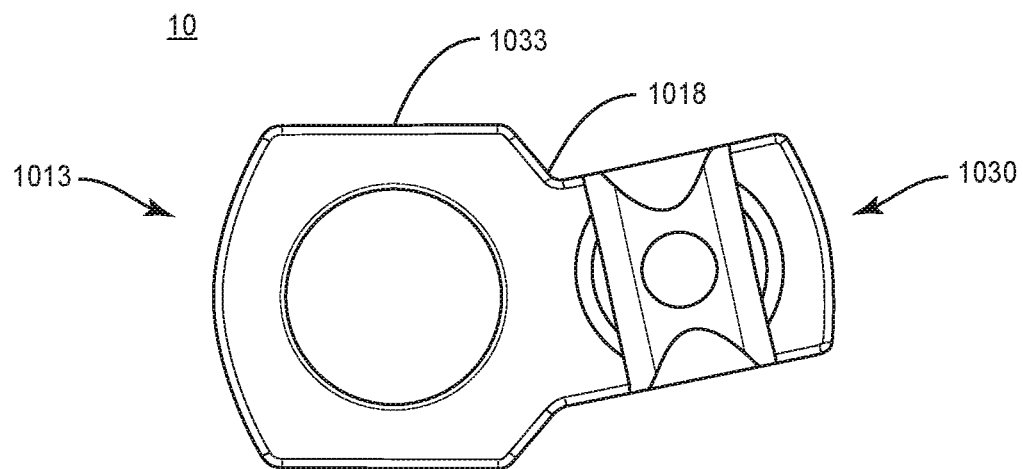
FIG. 42 is a plan view of components of one embodiment of a system in accordance with the principles of the present disclosure and FIG. 43 is a side view of components of one embodiment of a system in accordance with the principles of the present disclosure.

In one embodiment, as shown in FIG. 42, spinal implant system 10, similar to the systems and methods described herein, includes a connector 1013, similar to the connectors described herein, which can be employed with an existing spinal construct, similar to that described herein. Connector 1013 includes a sleeve 1033, similar to the sleeves described herein. Sleeve 1033 is configured for disposal of receiver 102 of fastener 100, as described herein. Connector 1013 includes an extension 1030 extending from a wall 1018. Extension 1030 is configured for disposal of rod 180, similar to that described herein, and oriented at an angle offset to sleeve 1033. In some embodiments, the angle of extension 1030 is disposed with a fixed angle in a coronal plane of a patient body.

Figure 43:
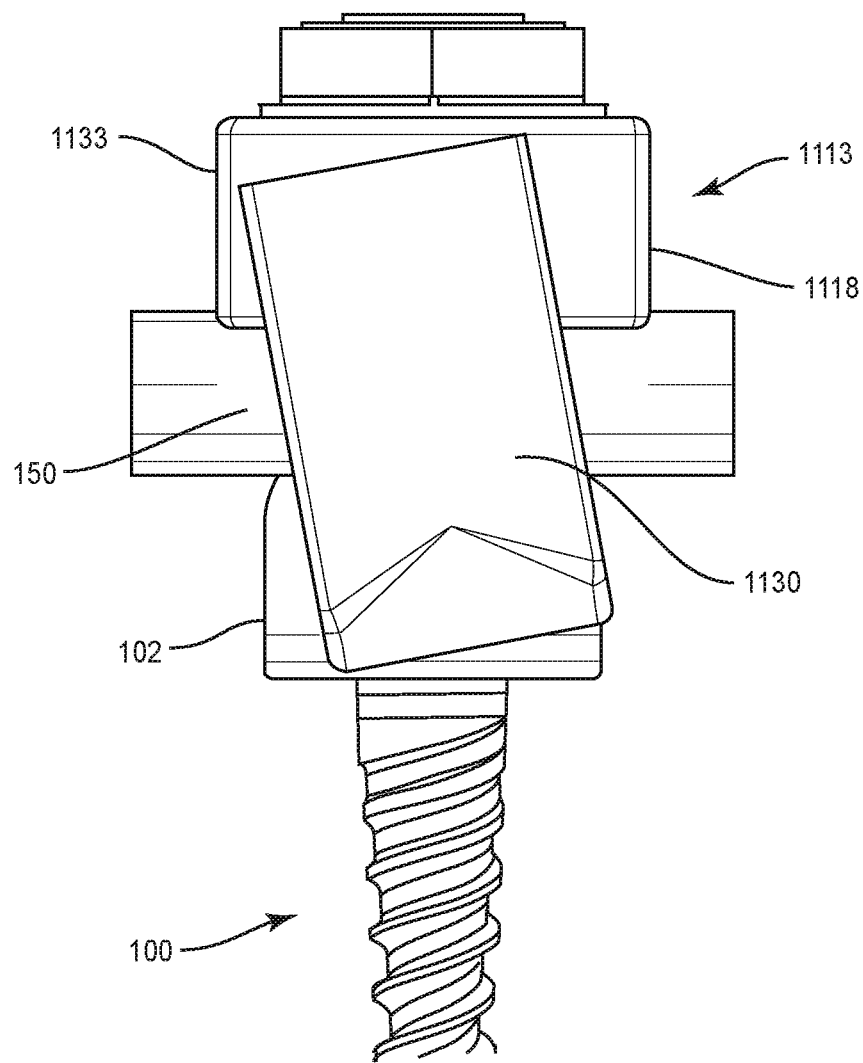

In one embodiment, as shown in FIG. 43, spinal implant system 10, similar to the systems and methods described herein, includes a connector 1113, similar to the connectors described herein, which can be employed with an existing spinal construct, similar to that described herein. Connector 1113 includes a sleeve 1133, similar to the sleeves described herein. Sleeve 1133 is configured for disposal of receiver 102 of fastener 100, as described herein. Connector 1113 includes an extension 1130 extending from a wall 1118. Extension 1130 is configured for disposal of rod 180, similar to that described herein, and oriented at an angle offset to sleeve 1133. In some embodiments, the angle of extension 1130 is disposed with a fixed angle in a sagittal plane of a patient body.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a connector comprising:
   a first body, the first body defining a central axis and having a wall, the wall defining a sleeve, a bore extending through the wall and co-axial with the central axis, the sleeve extending from a first surface to a second surface, the first surface having a planar configuration and extending perpendicular to the central axis, the sleeve includes an inner surface that defines a cavity, the cavity has a substantially rectangular cross-section, the cavity being configured for disposal of a receiver;
   a second body comprising an arm and a base extending transverse to the arm, the base being connected with an extension via a splined connection, the splined connection being moveable between an unlocked and a locked position, the wall being coupled to an outer surface of the arm, the outer surface of the arm being planar from the second surface of the sleeve to the base, the second body adapted to receive a first spinal rod, wherein the splined connection provides incremental and selective positioning of the first spinal rod;
   a set screw with a first mating surface and a second mating surface, the first mating surface configured for engagement with the receiver; and
   a nut comprising a tool engaging surface, a cavity configured for engagement with the second mating surface of the set screw, a circumferential flange, and a break off portion, wherein the nut is configured to engage the first surface to clamp the connector to the receiver.

2. The spinal construct recited in claim 1, wherein the arm includes an inner surface opposite the outer surface of the arm, the inner surface of the arm being concavely curved from the first surface to the base.

3. The spinal construct recited in claim 1, wherein the cavity of the sleeve is spaced apart from the second mating surface of the set screw.

4. The spinal construct recited in claim 1, wherein the flange directly engages the first surface.

5. The spinal construct recited in claim 1, wherein a planar distal surface of the flange directly engages the first surface.

6. The spinal construct recited in claim 1, wherein the the outer surface of the arm and inner surfaces of the first and second surfaces define the cavity.

7. The spinal construct recited in claim 1, wherein the spinal construct includes the extension, the extension extending parallel to the first surface.

8. The spinal construct recited in claim 1, wherein the spinal construct includes the extension, the extension including a proximal surface extending parallel to the first surface in a first plane and a distal surface extending from parallel to the first surface in a second plane that is offset from the first plane, the distal surface defining the splined connection.

9. The spinal construct recited in claim 8, wherein the distal surface directly engages the base.

10. The spinal construct recited in claim 1, wherein the second body comprises a threaded hole.

11. The spinal construct recited in claim 10, wherein the threaded hole extends parallel to the bore.

12. The spinal construct recited in claim 1, wherein the second surface includes first and second planar portions and a recess positioned between the planar portions.

13. The spinal construct recited in claim 12, wherein the receiver is configured for disposal of a second spinal rod, the recess being configured for disposal of a portion of the second spinal rod.

14. The spinal construct recited in claim 1, wherein the wall is a first wall and the spinal construct comprises a second wall that connects the first body with the second body.

15. The spinal construct recited in claim 14, wherein the second wall comprises a first side that directly engages the first wall and an opposite second side, the second side including a groove.

16. The spinal construct recited in claim 15, wherein the groove extends parallel to the bore.

17. The spinal construct recited in claim 1, wherein the base extends from a distal end of the arm such that the base extends perpendicular to the arm.

18. The spinal construct recited in claim 1, wherein the cavity of the nut is in communication with a passageway that extends through the break off portion.

19. A spinal construct comprising:
a connector comprising:
a first body, the first body defining a central axis and having a wall, the wall defining a sleeve, a bore extending through the wall and co-axial with the central axis, the sleeve extending from a first surface to a second surface, the first surface having a planar configuration and extending perpendicular to the central axis, the sleeve includes an inner surface that defines a cavity, the cavity has a substantially rectangular cross-section, the cavity being configured for disposal of a receiver, the receiver being configured for disposal of a first spinal rod;
an extension connected to the wall;
a second body comprising an arm and a base extending transverse to the arm, the base being connected with the extension via a splined connection, the splined connection being moveable between an unlocked and a locked position, the wall being coupled to an outer surface of the arm, the outer surface of the arm being planar from the second surface of the sleeve to the base, the second body adapted to receive a second spinal rod, wherein the splined connection provides incremental and selective positioning of the second spinal rod;
a set screw with a first mating surface and a second mating surface, the first mating surface configured for engagement with the receiver; and
a nut comprising a tool engaging surface, a cavity configured for engagement with the second mating surface of the set screw, a circumferential flange, and a break off portion, wherein the nut is configured to engage the first surface to clamp the connector to the receiver,
wherein the second body comprises a threaded hole, the threaded hole extending parallel to the bore, and
wherein the second surface includes first and second planar portions and a recess positioned between the planar portions, the recess being configured for disposal of a portion of the first spinal rod.

20. A spinal construct comprising:
a connector comprising:
a first body, the first body defining a central axis and having a wall, the wall defining a sleeve, a bore extending through the wall and co-axial with the central axis, the sleeve extending from a first surface to a second surface, the first surface having a planar configuration and extending perpendicular to the central axis, the sleeve includes an inner surface that defines a cavity, the cavity has a substantially rectangular cross-section, the cavity being configured for disposal of a receiver, the receiver being configured for disposal of a first spinal rod;
an extension connected to the wall;
a second body comprising an arm and a base extending transverse to the arm, the base being connected with the extension via a splined connection, the splined connection being moveable between an unlocked and a locked position, the wall being coupled to an outer surface of the arm, the outer surface of the arm being planar from the second surface of the sleeve to the base, the second body adapted to receive a second spinal rod, wherein the splined connection provides incremental and selective positioning of the second spinal rod;
a set screw with a first mating surface and a second mating surface, the first mating surface configured for engagement with the receiver; and
a nut comprising a tool engaging surface, a cavity configured for engagement with the second mating surface of the set screw, a circumferential flange, and a break off portion, the flange directly engaging the first surface, wherein the nut is configured to engage the first surface to clamp the connector to the receiver,
wherein the second wall comprises a first side that directly engages the first wall and an opposite second side, the second side including a groove, the groove extending parallel to the bore.

\* \* \* \* \*